United States Patent
Nishimura et al.

(10) Patent No.: US 11,156,598 B2
(45) Date of Patent: Oct. 26, 2021

(54) METHOD FOR EVALUATING CONTENT OF MESENCHYMAL STEM CELLS IN CELL-CONTAINING SAMPLE

(71) Applicant: Kaneka Corporation, Osaka (JP)

(72) Inventors: Akira Nishimura, Hyogo (JP); Masaru Nakatani, Hyogo (JP); Shigeo Furuyoshi, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 479 days.

(21) Appl. No.: 15/917,024

(22) Filed: Mar. 9, 2018

(65) Prior Publication Data

US 2018/0202994 A1 Jul. 19, 2018

Related U.S. Application Data

(63) Continuation-in-part of application No. PCT/JP2016/076647, filed on Sep. 9, 2016.

(30) Foreign Application Priority Data

Sep. 9, 2015 (JP) .............................. JP2015-177345

(51) Int. Cl.
| | |
|---|---|
| *C12Q 1/6881* | (2018.01) |
| *G01N 33/50* | (2006.01) |
| *A61K 35/28* | (2015.01) |
| *A61K 35/35* | (2015.01) |
| *C12Q 1/6876* | (2018.01) |

(52) U.S. Cl.
CPC ......... *G01N 33/5005* (2013.01); *A61K 35/28* (2013.01); *A61K 35/35* (2013.01); *C12Q 1/6876* (2013.01); *C12Q 1/6881* (2013.01); *G01N 33/5073* (2013.01); *C12Q 2600/154* (2013.01)

(58) Field of Classification Search
CPC .................. C12Q 1/6881; C12Q 2600/154
See application file for complete search history.

(56) References Cited

U.S. PATENT DOCUMENTS

2008/0293143 A1  11/2008  Lin et al.

FOREIGN PATENT DOCUMENTS

| JP | 2005-168486 A | 6/2005 |
| JP | 2014-166187 A | 9/2014 |

OTHER PUBLICATIONS

International Search Report issued in PCT/JP2016/076647; dated Oct. 11, 2016 (2 pages).
Yasuhiko Tabata, "Kokomade Susunda Saisei Iryo no Jissai (Actual State of Advanced Regenerative Medicine)" (2003); with partial English translation (9 pages).
Zuk et al., "Multilineage Cells from Human Adipose Tissue: Implications for Cell-Based Therapies", Tissue Engineering, vol. 7, No. 2, 2001, pp. 211-228 (18 pages).
Cao et al., "Human adipose tissue-derived stem cells differentiate into endothelial cells into vitro and improve postnatal neovascularization in vivo", Biochemical and Biophysical Research Communications 332 (2005) 370-379 (10 pages).
Philips et al., "Prevalence of Endogenous CD34+ Adipose Stem Cells Predicts Human Fat Graft Retention in a Xenograft Model", NIH Public Access, Author Manuscript, Plast Reconstr Surg. Oct. 2013, 132(4), pp. 845-858 (24 pages).
Boquest et al., "CpG Methylation Profiles of Endothelial Cell-Specific Gene Promoter Regions in Adipose Tissue Stem Dells Suggest Limited Differentiation Potential Toward the Endothelial Cell Lineage", Stem Cells, 2007, 25, pp. 852-861 (10 pages).
Nishimura et al., "Method for selective quantification of adipose-derived stromal/stem cells in tissue", Journal of Biological Methods, 2016, vol. 3(4), e58, pp. 1-5 (5 pages).

*Primary Examiner* — Diana B Johannsen
(74) *Attorney, Agent, or Firm* — Osha Bergman Watanabe & Burton LLP

(57) ABSTRACT

A method includes detecting a nucleotide sequence in genomic DNA obtained from a sample; and evaluating a content of mesenchymal stem cells in the sample. The nucleotide sequence comprises at least one CpG site selected from the group consisting of: a CpG site consisting of C at position 157 and G at position 158 of SEQ ID NO: 1; and a CpG site complementary to the CpG site of SEQ ID NO: 1 in a nucleotide sequence complementary to the nucleotide sequence of SEQ ID NO: 1. The sample is an adipose tissue or a cell-containing fraction obtained from an adipose tissue.

18 Claims, 1 Drawing Sheet

Specification includes a Sequence Listing.

CGAGACAGAG GGAGGGTCAA GAACGCCAAG GCAAATGTCA CTTGTGCCTT 50

GTTTTTCCC TAAAGAAACT AAACAAAGCG GCCGCGTTCG GTGGCCCCTC 100
SEQ ID NO: 2

AGGAAGGCCG GTCATTTCCT GAGGAGATAT CAGGCCCAGCC CAGGCCCCAT 150
                                                    SEQ ID NO: 3
         SEQ ID NO: 4

TGTTCCCGGT TTCCAGCCAT GGCTGCCATT ACCTGACCAG CGCCACAGCC 200
                                                    SEQ ID NO: 5
SEQ ID NO: 6

GGTCTCTCTG CAGGCGCCGG GAGAAGTGAC CAGAGCAATT TCTGCTTTTC 250
                      SEQ ID NO: 7
SEQ ID NO: 8

ACAGGGCGGG TTTCTCAACG GTGACTTGTG GGCAGTGCCT TCTGCTGAGC 300
                                          SEQ ID NO: 9

GAGTCATGGC CCGAAGGCAG AACTAACTGT GCCTGCAGTC TTCACTCTCA 350

GGATGCAGCC GAGGTGGGCC CAAGGGGCCA CGATGT 386

SEQUENCE LISTING

```
<160> NUMBER OF SEQ ID NOS: 9

<210> SEQ ID NO 1
<211> LENGTH: 386
<212> TYPE: DNA
<213> ORGANISM: Homo sapiens

<400> SEQUENCE: 1
cgagacagag ggagggtcaa gaacgccaag gcaaatgtca cttgtgcctt gttttttccc      60
```

```
taaagaaact aaacaaagcg gccgcgttcg gtggcccctc aggaaggccg gtcatttcct    120
gaggagatat caggccagcc caggccccat tgttcccggt ttccagccat ggctgccatt    180
acctgaccag cgccacagcc ggtctctctg caggcgccgg gagaagtgac cagagcaatt    240
tctgcttttc acagggcggg tttctcaacg gtgacttgtg ggcagtgcct tctgctgagc    300
gagtcatggc ccgaaggcag aactaactgt gcctgcagtc ttcactctca ggatgcagcc    360
gaggtgggcc caaggggcca cgatgt                                         386

<210> SEQ ID NO 2
<211> LENGTH: 18
<212> TYPE: DNA
<213> ORGANISM: Artificial
<220> FEATURE:
<223> OTHER INFORMATION: primer

<400> SEQUENCE: 2
ctaaagaaac taaacaaa                                                   18

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
cctgggctgg cctgatatc                                                  19

<210> SEQ ID NO 4
<211> LENGTH: 18
<212> TYPE: DNA
<213> ORGANISM: Artificial
<220> FEATURE:
<223> OTHER INFORMATION: primer

<400> SEQUENCE: 4
ggagatatca ggccagcc                                                   18

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
tggcgctggt caggtaat                                                   18

<210> SEQ ID NO 6
<211> LENGTH: 17
<212> TYPE: DNA
<213> ORGANISM: Artificial
<220> FEATURE:
<223> OTHER INFORMATION: primer

<400> SEQUENCE: 6
agccatggct gccatta                                                    17

<210> SEQ ID NO 7
<211> LENGTH: 15
<212> TYPE: DNA
<213> ORGANISM: Artificial
<220> FEATURE:
<223> OTHER INFORMATION: primer
```

```
<400> SEQUENCE: 7
gcgcctgcag agaga                                                    15

<210> SEQ ID NO 8
<211> LENGTH: 15
<212> TYPE: DNA
<213> ORGANISM: Artificial
<220> FEATURE:
<223> OTHER INFORMATION: primer

<400> SEQUENCE: 8
tctctctgca ggcgc                                                    15

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
cccacaagtc accgttga                                                 18
```

METHOD FOR EVALUATING CONTENT OF MESENCHYMAL STEM CELLS IN CELL-CONTAINING SAMPLE

This application is a continuation-in-part of PCT International Application PCT/JP2016/076647 filed Sep. 9, 2016, which in turns claims benefit of Japanese Patent Application No. 2015-177345, the entire contents of each of which is incorporated herein by reference.

TECHNICAL FIELD

The present invention relates to a method for evaluating the content of mesenchymal stem cells in a sample containing cells, a kit used to evaluate the content of mesenchymal stem cells in a sample containing cells, and a method for producing a mesenchymal stem cell-containing formulation from a sample containing cells.

BACKGROUND ART

Mesenchymal stem cells (MSCs) are somatic stem cells present in the adipose tissues, bone marrow and the like of mammals. In recent years, it has been revealed that, among such mesenchymal stem cells, stem cells having ability to differentiate not only into cells of the same tissue strain, but also into cells of a different strain, are present (Non Patent Literature 1). For example, mesenchymal stem cells collected from adipose tissues are able to differentiate, not only into mature adipocytes, but also into bone cells, chondrocytes, myoblasts, vascular endothelial cells, and the like (Non Patent Literatures 2 and 3). It is anticipated that mesenchymal stem cells will be applied to regenerative medicine, such as reconstruction of bone, blood vessel, and heart muscle.

CITATION LIST

Non Patent Literature

Non Patent Literature 1: Yasuhiko TABATA, "Kokomade Susunda Saisei Iryo no Jissai (Actual State of Advanced Regenerative Medicine)" (2003)
Non Patent Literature 2: Patricia A. Zuk, et al.: Multilineage cells from human adipose tissue: Implications for cell-based therapies. Tissue Engineering Vol. 7(2).: 211-228 (2001).
Non Patent Literature 3: Ying Cao, et al.: Human adipose tissue-derived stem cells differentiate into endothelial cells in vitro and improve postnatal neovascularization in vivo. Biochemical and Biophysical Research Communications 332: 370-379 (2005).
Non Patent Literature 4: Plast Reconstr Surg. 2013, October; 132(4).: 845-858

SUMMARY OF INVENTION

Technical Problem

The amount of mesenchymal stem cells in a cell-containing sample such as a biological sample, which is used in regenerative medicine or the like, is information that is important for determining a method of using the sample or the use amount thereof. For example, in breast enlargement surgery, breast reconstruction or the like, which involves transplantation of adipose tissues obtained by liposuction or the like, the survival percentage of the transplanted adipose tissues has a proportional relationship with the content of mesenchymal stem cells in the adipose tissues (Non Patent Literature 4). Thus, if the content of mesenchymal stem cells in adipose tissues can be obtained, the appropriate amount of adipose tissues transplanted or the number of transplantations can be precisely determined based on the obtained content. In addition, in a case where a stromal vascular fraction (SVF), which is a cell fraction derived from adipose tissues other than adipocytes, is separated from adipose tissues, and the obtained SVF is used in breast enlargement surgery or cell therapy for ischemic disease, etc., or in a case where SVF is cultured to produce high-purity mesenchymal stem cells, and the obtained mesenchymal stem cells are also used in breast enlargement surgery or cell therapy, if the content of mesenchymal stem cells in adipose tissues as starting raw material could have been known in advance, the amount of SVF that can be obtained from the adipose tissues or the amount of high-purity mesenchymal stem cells can be precisely predicted. Moreover, conditions for obtaining SVF or high-purity mesenchymal stem cells from the adipose tissues (e.g., culture conditions, etc.) can be easily determined.

Thus, if the amount of mesenchymal stem cells in a sample to be used can be grasped, it would greatly contribute to the development of a technique of applying mesenchymal stem cells. As a method of quantifying mesenchymal stem cells, a method comprising preparing a dispersion in which mesenchymal stem cells are dispersed and then measuring the number of mesenchymal stem cells using a flow cytometer (flow cytometry) has been conventionally known. However, in the case of flow cytometry, the amount of mesenchymal stem cells in a sample such as adipose tissues cannot be directly measured, and thus, it is necessary to isolate cells from the sample and then to prepare a dispersion thereof. Also, such flow cytometry provides low sensitivity. Accordingly, this method still has room for improvement.

Hence, it is an object of the present invention to provide a method for directly evaluating the content of mesenchymal stem cells in various forms of cell-containing samples, such as adipose tissues, and a related technique thereof.

Solution to Problem

The present invention provides the following inventions as means for achieving the above-described object.

(1)

A method for evaluating the content of mesenchymal stem cells in a sample containing cells, said method comprising a nucleic acid detection step of detecting a nucleotide sequence comprising at least one CpG site that has been methylated at a higher percentage in mesenchymal stem cells than in other cells, in the nucleotide sequence of CD31 promoter or a complementary strand thereof, comprised in genomic DNA obtained from the sample.

(2)

The method according to the above (1), wherein the ratio (B/A) between the percentage A (%) of the CpG site methylated in CD31 promoter derived from mesenchymal stem cells or a complementary strand thereof and the percentage B (%) of the CpG site methylated in CD31 promoter derived from other cells or a complementary strand thereof is 0.75 or less.

(3)

The method according to the above (1) or (2), wherein the CpG site is any one or more of:

a CpG site consisting of C at position 109 and G at position 110 of SEQ ID NO: 1, a CpG site complementary to the CpG site consisting of C at position 109 and G at position 110 of SEQ ID NO: 1, in a nucleotide sequence complementary to the nucleotide sequence of SEQ ID NO: 1, a CpG site consisting of C at position 157 and G at position 158 of SEQ ID NO: 1, a CpG site complementary to the CpG site consisting of C at position 157 and G at position 158 of SEQ ID NO: 1, in a nucleotide sequence complementary to the nucleotide sequence of SEQ ID NO: 1, a CpG site consisting of C at position 200 and G at position 201 of SEQ ID NO: 1, a CpG site complementary to the CpG site consisting of C at position 200 and G at position 201 of SEQ ID NO: 1, in a nucleotide sequence complementary to the nucleotide sequence of SEQ ID NO: 1, a CpG site consisting of C at position 218 and G at position 219 of SEQ ID NO: 1, and a CpG site complementary to the CpG site consisting of C at position 218 and G at position 219 of SEQ ID NO: 1, in a nucleotide sequence complementary to the nucleotide sequence of SEQ ID NO: 1.

(4)

The method according to any one of the above (1) to (3), wherein the nucleic acid detection step comprises selectively detecting the amount of DNA comprising a nucleotide sequence comprising said at least one CpG site that has been methylated, in the nucleotide sequence of the CD31 promoter or the complementary strand thereof, or selectively detecting the amount of DNA comprising a nucleotide sequence comprising said at least one CpG site that has not been methylated, in the nucleotide sequence of the CD31 promoter or the complementary strand thereof.

(5)

The method according to any one of the above (1) to (4), wherein the nucleic acid detection step is a nucleic acid detection step of detecting a nucleotide sequence comprising said at least one CpG site in the nucleotide sequence of the CD31 promoter or the complementary strand thereof, by performing a restriction enzyme treatment and/or a nucleic acid amplification treatment.

(6)

The method according to the above (5), wherein the restriction enzyme used in the restriction enzyme treatment is an enzyme specifically cleaving only the methylated nucleotide sequence, or an enzyme that has CCGG as a recognition sequence and cannot cleave the methylated nucleotide sequence.

(7)

The method according to any one of the above (1) to (6), wherein the sample containing cells is a cell culture liquid, adipose tissues, a bone marrow fluid, peripheral blood, chorion, placenta or amnion, or a cell-containing sample obtained from at least one of these samples.

(8)

The method according to any one of the above (1) to (7), wherein said other cells are any one or more selected from leucocytes, erythrocytes, monocytes, vascular endothelial cells, pericytes, mature adipocytes, and epithelial cells.

(9)

A method for producing a mesenchymal stem cell-containing formulation from a sample containing cells, said method comprising:

a sample selection step of detecting a nucleotide sequence comprising at least one CpG site that has been methylated at a higher percentage in mesenchymal stem cells than in other cells, in the nucleotide sequence of CD31 promoter or a complementary strand thereof, comprised in genomic DNA obtained from the sample, and then selecting the sample to be used in the production of the formulation based on the detection results; and a formulation production step of producing the formulation from the selected sample.

(10)

The method according to the above (9), wherein the ratio (B/A) between the percentage A (%) of the CpG site methylated in CD31 promoter derived from mesenchymal stem cells or a complementary strand thereof and the percentage B (%) of the CpG site methylated in CD31 promoter derived from other cells or a complementary strand thereof is 0.75 or less.

(11)

The method according to the above (9) or (10), wherein the CpG site is any one or more selected from:

a CpG site consisting of C at position 109 and G at position 110 of SEQ ID NO: 1, a CpG site complementary to the CpG site consisting of C at position 109 and G at position 110 of SEQ ID NO: 1, in a nucleotide sequence complementary to the nucleotide sequence of SEQ ID NO: 1, a CpG site consisting of C at position 157 and G at position 158 of SEQ ID NO: 1, a CpG site complementary to the CpG site consisting of C at position 157 and G at position 158 of SEQ ID NO: 1, in a nucleotide sequence complementary to the nucleotide sequence of SEQ ID NO: 1, a CpG site consisting of C at position 200 and G at position 201 of SEQ ID NO: 1, a CpG site complementary to the CpG site consisting of C at position 200 and G at position 201 of SEQ ID NO: 1, in a nucleotide sequence complementary to the nucleotide sequence of SEQ ID NO: 1, a CpG site consisting of C at position 218 and G at position 219 of SEQ ID NO: 1, and a CpG site complementary to the CpG site consisting of C at position 218 and G at position 219 of SEQ ID NO: 1, in a nucleotide sequence complementary to the nucleotide sequence of SEQ ID NO: 1.

(12)

The method according to any one of the above (9) to (11), wherein the sample selection step comprises selectively detecting the amount of DNA comprising a nucleotide sequence comprising said at least one CpG site that has been methylated, in the nucleotide sequence of the CD31 promoter or the complementary strand thereof, or selectively detecting the amount of DNA comprising a nucleotide sequence comprising said at least one CpG site that has not been methylated, in the nucleotide sequence of the CD31 promoter or the complementary strand thereof.

(13)

The method according to any one of the above (9) to (12), wherein the sample selection step is a sample selection step of detecting a nucleotide sequence comprising said at least one CpG site in the nucleotide sequence of the CD31 promoter or the complementary strand thereof, by performing a restriction enzyme treatment and/or a nucleic acid amplification treatment, and then selecting the sample to be used in the production of the formulation based on the detection results.

(14)

The method according to the above (13), wherein the restriction enzyme used in the restriction enzyme treatment is an enzyme specifically cleaving only the methylated nucleotide sequence, or an enzyme that has CCGG as a recognition sequence and cannot cleave the methylated nucleotide sequence.

(15)

A kit for evaluating the content of mesenchymal stem cells in a sample containing cells, said kit comprising a primer set capable of amplifying a region comprising any one or more selected from: a CpG site consisting of C at position 109 and G at position 110, a CpG site consisting of C at position 157 and G at position 158, a CpG site consisting of C at position 200 and G at position 201, and a CpG site consisting of C at position 218 and G at position 219, in the nucleotide sequence of CD31 promoter shown in SEQ ID NO: 1; and a CpG site complementary to the CpG site consisting of C at position 109 and G at position 110 in the nucleotide sequence of SEQ ID NO: 1, a CpG site complementary to the CpG site consisting of C at position 157 and G at position 158 in the nucleotide sequence of SEQ ID NO: 1, a CpG site complementary to the CpG site consisting of C at position 200 and G at position 201 in the nucleotide sequence of SEQ ID NO: 1, and a CpG site complementary to the CpG site consisting of C at position 218 and G at position 219 in the nucleotide sequence of SEQ ID NO: 1, in a nucleotide sequence complementary to the nucleotide sequence of CD31 promoter shown in SEQ ID NO: 1.

(16)

The kit according to the above (15), further comprising bisulfite and deoxyribonucleotide triphosphate.

(17)

The kit according to the above (15) or (16), further comprising a restriction enzyme.

(18)

A method for treating a subject in need of the treatment of disease or disorder, using a mesenchymal stem cell-containing formulation, said method comprising a step of administering a mesenchymal stem cell-containing formulation obtained by the method according to any one of the above (9) to (14) to a subject having disease or disorder.

(19)

A method for treating a subject in need of the treatment of disease or disorder, using mesenchymal stem cells, said method comprising a step of administering mesenchymal stem cells derived from a sample containing cells that has been evaluated to comprise mesenchymal stem cells by the method according to the above (1) to (8), to a subject having disease or disorder.

The present description includes part or all of the contents as disclosed in Japanese Patent Application No. 2015-177345, which is a priority document of the present application.

Advantageous Effects of Invention

According to the present invention, there is provided a means for directly evaluating the content of mesenchymal stem cells in various forms of cell-containing samples such as adipose tissues. In addition, since the content of mesenchymal stem cells can be grasped in advance according to the means for directly evaluating the content of mesenchymal stem cells of the present invention, the appropriate dose of the mesenchymal stem cells and the number of administrations thereof can be precisely determined, and thus, the time and labor of administration, costs, burden on a subject, etc. can be reduced.

BRIEF DESCRIPTION OF DRAWINGS

FIG. 1 shows: a CpG sequence containing methylated cytosine (C) in the DNA nucleotide sequence (SEQ ID NO: 1) of a CD promoter comprised in the genomic DNA of human adipose tissue-derived mesenchymal stem cells (ASCs) with an underlined portion; and CCGG that is a recognition sequence of restriction enzymes HapII and MspI with bold letters. FIG. 1 indicates a position corresponding to each primer consisting of the nucleotide sequence shown in any one of SEQ ID NOS: 2 to 9. A forward primer and a reverse primer comprised as a pair in one primer set are shown with the same line type.

DESCRIPTION OF EMBODIMENTS

<Materials>

In the present invention, the terms "cells," "a sample containing cells," "mesenchymal stem cells," and "genomic DNA" typically indicate those derived from humans. However, these may also be derived from other animals, and examples of such other animals include mammals such as a dog, a cat, a bovine, a horse, a swine, sheep, a monkey or a ferret, and birds such as a chicken. When a sample containing cells used in the present invention is a sample derived from the above-described animals, a sample that has been separated from the above-described animals can be used in the method of the present invention.

The "sample containing cells" is not particularly limited, as long as it is a sample, which contains cells and is also likely to contain mesenchymal stem cells. Examples of the sample containing cells include a cell culture liquid, adipose tissues, a bone marrow fluid, peripheral blood, chorion, placenta, amnion, and a cell-containing sample obtained from at least one of these samples (e.g., a cell-containing fraction), and also, a cell-containing sample prepared by mixing two or more of these samples (e.g., a sample prepared by mixing adipose tissues with mesenchymal stem cells). Among these, adipose tissues or cell-containing fractions obtained from such adipose tissues are particularly preferable. An example of such a cell-containing fraction obtained from adipose tissues can be a stromal vascular fraction (SVF) that is a cell fraction derived from adipose tissues comprising cells other than adipocytes. SVF may comprise remaining adipocytes.

In the present invention, the term "other cells" indicates cells other than mesenchymal stem cells, which are likely to be contained in a sample as an evaluation subject. Besides, cells other than mesenchymal stem cells, which are likely to be contained in a trace amount in the sample as an evaluation subject, for example, cells contained at a percentage of less than 0.5%, and typically less than 0.1%, relative to the number of cells, in the total number of cells in a sample, are not considered to be such "other cells." The types of such "other cells" are different depending on the sample. Examples of such other cells include one or more selected from blood-derived cells (specifically, leucocytes, erythrocytes, monocytes, etc.), vascular endothelial cells, pericytes, mature adipocytes, and epithelial cells.

<Method for Evaluating the Content of Mesenchymal Stem Cells>

In the present invention, in a nucleic acid detection step, a nucleotide sequence comprising at least one CpG site that has been methylated at a higher percentage in mesenchymal stem cells than in other cells, in the nucleotide sequence of CD31 promoter or a complementary strand thereof, comprised in genomic DNA obtained from a cell-containing sample, is detected, and thereafter, the detected nucleotide sequence is used as an indicator to evaluate the content of mesenchymal stem cells. The method for evaluating the content of mesenchymal stem cells of the present invention is considered to be a method which also comprises an evaluation step of evaluating the content of mesenchymal stem cells in the sample, using the detection results as an indicator, in addition to the above-described nucleic acid detection step of detecting a nucleotide sequence comprising at least one CpG site that has been methylated at a higher percentage in mesenchymal stem cells than in other cells, in the nucleotide sequence of CD31 promoter or a complementary strand thereof, comprised in genomic DNA obtained from a cell-containing sample.

Herein, the phrase "evaluate the content" of mesenchymal stem cells comprehensively indicates that the detection results obtained in the nucleic acid detection step are utilized as an indicator that reflects the content of mesenchymal stem cells in the sample (which may be an absolute amount such as cell count or weight, or may also be a relative amount (rate)), and thus, the phrase is not limited to a specific embodiment. For example, utilization of the detection results themselves as an indicator reflecting the content of mesenchymal stem cells (in this case, the content of mesenchymal stem cells itself does not need to be obtained), or the obtaining of the content of mesenchymal stem cells from the detection results obtained in the nucleic acid detection step, based on the correlation of the detection results of the nucleic acid detection step with the content of mesenchymal stem cells, or the like corresponds to the "evaluation of the content" of mesenchymal stem cells.

The nucleotide sequence of CD31 promoter in human-derived genomic DNA comprises the nucleotide sequence shown in SEQ ID NO: 1. The nucleotide sequence of a complementary strand of the CD31 promoter in human-derived genomic DNA is a nucleotide sequence complementary to the nucleotide sequence shown in SEQ ID NO: 1.

A method of obtaining genomic DNA from a cell-containing sample is not particularly limited. For example, genomic DNA can be obtained by being extracted from a cell-containing sample. The extraction method is not particularly limited, and genomic DNA can be extracted using a commercially available DNA extraction kit, in accordance with the instruction manual included with the kit. Such a commercially available DNA extraction kit can be, for example, DNeasy Plant Mini Kit (QIAGEN).

In the nucleic acid detection step, a nucleotide sequence comprising at least one CpG site that has been methylated at a higher percentage in mesenchymal stem cells than in other cells, in CD31 promoter or a complementary strand thereof in genomic DNA, is detected. In the present invention, detection of a certain nucleotide sequence indicates detection of a nucleic acid (which is, generally, DNA) comprising the nucleotide sequence, and more preferably, consisting of the nucleotide sequence.

The CpG site is a dibasic structure consisting of a cytosine (C) and a guanine (G) ligated to the 3'-terminal side of the cytosine in a nucleic acid molecule. The letter "p" means a phosphodiester bond between the cytosine and the guanine.

Methylation of the CpG site indicates methylation of cytosine in the CpG site. It is considered that methylation of the CpG site in genomic DNA is associated with differentiation of cells, etc. The present invention is an invention, in which a phenomenon whereby a specific CpG site contained in the nucleotide sequence of CD31 promoter in genomic DNA has been methylated at a higher percentage in mesenchymal stem cells than in other cells is utilized, and the methylation of the specific CpG site is used as an indicator for the mesenchymal stem cells.

The above-described CpG site is not particularly limited, as long as it is a CpG site contained in the nucleotide sequence of CD31 promoter in genomic DNA or a complementary strand thereof, wherein the CpG site has been methylated at a higher percentage in mesenchymal stem cells than in other cells. It is particularly preferably a CpG site, regarding which when the percentage of the CpG site methylated in CD31 promoter derived from mesenchymal stem cells is defined as A (%) and when the percentage of the CpG site methylated in CD31 promoter derived from other cells is defined as B (%), the ratio (B/A) is 0.75 or less.

In a case where adipose tissues are used as a sample, among a CpG site(s) in CD31 promoter comprised in genomic DNA obtained from the adipose tissues, the percentage of CpG sites methylated in CD31 promoter derived from mesenchymal stem cells is defined as A %, the percentage of CpG sites methylated in CD31 promoter derived from vascular endothelial cells is defined as $B_1$%, the percentage of CpG sites methylated in CD31 promoter derived from pericytes is defined as $B_2$%, the percentage of CpG sites methylated in CD31 promoter derived from blood-derived cells is defined as $B_3$%, and the percentage of CpG sites methylated in CD31 promoter derived from mature adipocytes is defined as $B_4$%. In this case, $B_1$/A is 0.75 or less, and preferably 0.20 or less; $B_2$/A is 0.75 or less, and preferably 0.30 or less; $B_3$/A is 0.34 or less, and preferably 0.10 or less; and $B_4$/A is 0.75 or less, and preferably 0.45 or less. The CpG site satisfying the aforementioned conditions is adopted as a CpG site as described above.

When a stromal vascular fraction (SVF) is used as a sample, a CpG site, which satisfies $B_1$/A of 0.75 or less, and preferably 0.20 or less, $B_2$/A of 0.75 or less, and preferably 0.30 or less, and $B_3$/A of 0.34 or less, and preferably 0.10, is preferably adopted as a CpG site as described above.

Specifically, the above-described CpG site in the nucleotide sequence (SEQ ID NO: 1) of CD31 promoter in genomic DNA is one or more selected from the following CpG site group: a CpG site consisting of C at position 109 and G at position 110 (which is referred to as "C109-G110," and so forth), C157-G158, C200-G201, C218-G219, C79-G80, C85-G86, C191-G192, C215-G216, C257-G258, C269-G270, C1-G2, C24-G25, C83-G84, C89-G90, C300-G301, C312-G313, C360-G361, and C381-G382. The CpG site is preferably one or more selected from the group consisting of C109-G110, C157-G158, C200-G201, C218-G219, C79-G80, C85-G86, C191-G192, C215-G216, C257-G258, and C269-G270; more preferably one or more selected from the group consisting of C109-G110, C157-G158, C200-G201, and C218-G219; further preferably one or more selected from the group consisting of C157-G158, C200-G201, and C218-G219; and most preferably C157-G158.

Likewise, as a CpG site in the nucleotide sequence of a complementary strand of the CD31 promoter in genomic DNA, a complementary CpG site corresponding to each of the above-described CpG sites in the nucleotide sequence shown in SEQ ID NO: 1 is preferable.

In the nucleic acid detection step of the present invention, DNA comprising a nucleotide sequence comprising at least one of the above-described CpG sites (preferably, DNA consisting of a nucleotide sequence comprising at least one of the above-described CpG sites), in the nucleotide sequence of CD31 promoter or a complementary strand thereof, comprised in genomic DNA (hereinafter referred to as "sample DNA") obtained from a sample, is detected. More specifically, in the nucleic acid detection step of the present invention, the amount of DNA comprising a nucleotide sequence comprising at least one of the above-described CpG sites, in which the CpG site has been methylated, in the CD31 promoter or a complementary strand thereof comprised in sample DNA, or the amount of DNA comprising a nucleotide sequence comprising at least one of the above-described CpG sites, in which the CpG site has not been methylated, is selectively detected.

Herein, detection of the amount of certain DNA is not limited to the measurement of the amount of desired DNA comprised in sample DNA, or calculation of the aforementioned amount, but it totally includes the obtaining of data that reflect the amount of desired DNA in sample DNA. For example, when sample DNA is used as a template in a nucleic acid amplification reaction of amplifying desired DNA, examples of such data include the number of amplification reaction cycles necessary for reaching the amount of an amplification product used as a threshold (Ct value), and the pattern or density of a band obtained by subjecting an amplification product to gel electrophoresis. Alternatively, the amount of desired DNA may also be detected based on the pattern or density of a band obtained by subjecting sample DNA treated with restriction enzyme to gel electrophoresis, without performing a nucleic acid amplification reaction. When the sample is sufficiently evaluated by obtaining such data, it is not necessary to calculate the amount of desired DNA in sample DNA.

Examples of a means for selectively detecting the amount of DNA comprising a nucleotide sequence in which the CpG site has been methylated, or the amount of DNA comprising a nucleotide sequence in which the CpG site has not been methylated, in sample DNA, include the following means.

<Selective Detection Method 1>

An example of selective detection method 1 is a method which comprises treating sample DNA with an enzyme cleaving a DNA molecule at a CpG site or in a vicinity thereof, when the CpG site has not been methylated, and then detecting the amount of DNA comprising the nucleotide sequence of CD31 promoter or a complementary strand thereof, in which the CpG site has been methylated, in the sample DNA after completion of the treatment. Specifically, this is a method comprising performing a nucleic acid amplification reaction using the sample DNA after completion of the treatment as a template and a primer set capable of amplifying a nucleotide sequence comprising a site to be cleaved by the enzyme present in the nucleotide sequence of CD31 promoter or a complementary strand thereof, and then quantifying the nucleic acid molecule amplified by the reaction. According to this method, the amount of DNA comprising the nucleotide sequence of CD31 promoter or a complementary strand thereof, in which the above-described CpG site has been methylated, can be selectively detected in the sample DNA. Besides, the method for detecting the amount of DNA comprising the nucleotide sequence of CD31 promoter or a complementary strand thereof, in which the above-described CpG site has been methylated, in the sample DNA after completion of the treatment with the enzyme, is not limited to a method involving a nucleic acid amplification reaction, and for example, the amount of DNA comprising the nucleotide sequence of CD31 promoter or a complementary strand thereof, in which the above-described CpG site has been methylated, may be detected based on the pattern or density of a band obtained by subjecting the enzyme-treated sample DNA to gel electrophoresis.

Moreover, as a control test, the total amount of DNA comprising the above-described CpG site is detected in untreated sample DNA that has not been treated with the above-described enzyme. Specifically, untreated sample DNA that has not been treated with the above-described enzyme is used as a template, and a nucleic acid amplification reaction is carried out under the same conditions as those described above. The nucleic acid molecule amplified by the reaction is quantified, so that the total amount of DNA comprising the above-described CpG site in the sample DNA can be detected regardless of the presence or absence of methylation. The method of detecting the total amount of DNA comprising the above-described CpG site in untreated sample DNA is not limited to a method involving a nucleic acid amplification reaction. For example, based on the pattern and density of a band obtained by subjecting untreated sample DNA to gel electrophoresis, the total amount of DNA comprising the above-described CpG site may be detected. Based on a difference between the total amount of DNA comprising the above-described CpG site obtained in the control test and the amount of DNA comprising the methylated CpG site obtained in the test of the above paragraph, the amount of DNA comprising the unmethylated CpG site can be selectively detected.

The enzyme that selectively cleaves a nucleotide sequence comprising the above-described unmethylated CpG site can be an enzyme, the recognition sequence of which is CCGG, and which can cleave the CCGG when the CpG site comprised in the CCGG has not been methylated, but cannot cleave the CCGG when the CpG site comprised in the CCGG has been methylated. More specific examples of such enzyme include HapII and HpaII. HapII is purified from an *Escherichia coli* strain having a HapII gene cloned from *Haemophilus aphrophilus*, and this enzyme is available from Takara Bio, Inc. For details of HapII, please refer to Sugisaki H. and Takanami M., Nature New Biol. 246, 138-140, 1973. HpaII is purified from an *Escherichia coli* strain having a HpaII gene cloned from *Haemophilus parainfluenzae*, and this enzyme is available from New England Biolabs Japan Inc. For details of HpaII, please refer to Card et al., Nucleic Acids Res. 25, 1377-1383, 1990.

Selective detection method 1 is particularly suitable for the case of selectively detecting the amount of DNA comprising a nucleotide sequence, in which one or more CpG sites selected from C109-G110, C157-G158, C200-G201 and C218-G219 in sample DNA, or complementary CpG sites corresponding to one or more CpG sites selected from C109-G110, C157-G158, C200-G201 and C218-G219 of CD31 promoter in the nucleotide sequence of a complementary strand of the CD31 promoter, have been methylated or have not been methylated. These CpG sites are comprised in the CCGG sequence.

<Selective Detection Method 2>

An example of selective detection method 2 is a method which comprises treating sample DNA with an enzyme cleaving a DNA molecule at a CpG site or in a vicinity thereof, when the CpG site has been methylated, and then detecting the amount of DNA comprising the nucleotide sequence of CD31 promoter or a complementary strand thereof, in which the CpG site has not been methylated, in the sample DNA after completion of the treatment. Specifically, this is a method comprising performing a nucleic acid amplification reaction using the sample DNA after completion of the treatment as a template and a primer set capable of amplifying a nucleotide sequence comprising a site to be cleaved by the enzyme present in the nucleotide sequence of CD31 promoter or a complementary strand thereof, and then quantifying the nucleic acid molecule amplified by the reaction. According to this method, the amount of DNA comprising the nucleotide sequence of CD31 promoter or a complementary strand thereof, in which the above-described CpG site has not been methylated, can be selectively detected in the sample DNA. Besides, the method for detecting the amount of DNA comprising the nucleotide sequence of CD31 promoter or a complementary strand thereof, in which the above-described CpG site has not been methylated, in the sample DNA after completion of the treatment with the enzyme, is not limited to a method involving a nucleic acid amplification reaction, and for example, the amount of DNA comprising the nucleotide sequence of CD31 promoter or a complementary strand thereof, in which the above-described CpG site has not been methylated, may be detected based on the pattern or density of a band obtained by subjecting the enzyme-treated sample DNA to gel electrophoresis.

Moreover, as a control test, the total amount of DNA comprising the above-described CpG site is detected in untreated sample DNA that has not been treated with the above-described enzyme. Specifically, untreated sample DNA that has not been treated with the above-described enzyme is used as a template, and a nucleic acid amplification reaction is carried out under the same conditions as those described above. The nucleic acid molecule amplified by the reaction is quantified, so that the total amount of DNA comprising the above-described CpG site in the sample DNA can be detected regardless of the presence or absence of methylation. As with the control test in the above-described selective detection method 1, the method of detecting the total amount of DNA comprising the above-described CpG site in untreated sample DNA is not limited to a method involving a nucleic acid amplification reaction. Based on a difference between the total amount of DNA comprising the above-described CpG site obtained in the control test and the amount of DNA comprising the unmethylated CpG site obtained in the test of the above paragraph, the amount of DNA comprising the methylated CpG site can be selectively detected.

A commercially available enzyme that specifically cleaves only the nucleotide sequence comprising the methylated CpG site is, for example, McrBC. McrBC is a complex of McrB and McrC, and is purified from an *Escherichia coli* strain having McrB and McrC genes encoding McrB and McrC. McrBC is available from New England Biolabs Japan Inc., etc. For details of McrBC, please refer to Ellen et al., J. Mol. Biol. 225, 327-348, 1992.

<Selective Detection Method 3>

As selective detection method 3, sample DNA is treated with bisulfite, so that cytosine in the unmethylated CpG site in the sample DNA is converted to uracil. Thereafter, a nucleotide sequence comprising the above-described CpG site in the nucleotide sequence of CD31 promoter or a complementary strand thereof in the bisulfite-treated sample DNA is analyzed by performing a sequence analysis or a restriction enzyme treatment, so that the amount of DNA comprising a nucleotide sequence containing the methylated CpG site or DNA comprising a nucleotide sequence containing the unmethylated CpG site can be selectively detected in the sample DNA. A specific example of this method is a method comprising performing a nucleic acid amplification reaction using bisulfite-treated sample DNA as a template and a primer set capable of amplifying a nucleotide sequence comprising the above-described CpG site present in the nucleotide sequence of CD31 promoter or a complementary strand thereof, and then analyzing the nucleic acid molecule amplified by the reaction. If the nucleotide corresponding to C in the above-described CpG site is cytosine in the sense strand and is guanine in the antisense strand in the nucleic acid molecule amplified by the above-described reaction, this nucleic acid molecule is an amplification product of DNA comprising the methylated CpG site. On the other hand, if the nucleotide corresponding to C in the above-described CpG site is thymine in the sense strand and is adenine in the antisense strand in the nucleic acid molecule amplified by the above-described reaction, this nucleic acid molecule is an amplification product of DNA comprising the unmethylated CpG site. Accordingly, the nucleic acid molecule amplified by the above-described reaction of selective detection method 3 is analyzed by performing a sequence analysis or a restriction enzyme treatment, so that the amount of DNA comprising a nucleotide sequence containing the methylated CpG site or DNA comprising a nucleotide sequence containing the unmethylated CpG site can be selectively detected in the sample DNA.

Hereafter, explanation of the present invention will be continued.

Examples of a primer set capable of amplifying a nucleotide sequence comprising at least one of the above-described CpG sites in the nucleotide sequence of CD31 promoter or a complementary strand thereof in sample DNA, which can be used in the nucleic acid detection step of the present invention, include the below-described primer sets. The polynucleotide in each primer set can be, for example, DNA.

For example, as a primer set for amplifying a nucleotide sequence comprising at least one CpG site that is present in the range from positions 1 to 156 of SEQ ID NO: 1, in the nucleotide sequence of CD31 promoter in sample DNA, the below-described primer set (I) is preferable.

In addition, also as a primer set for amplifying a nucleotide sequence complementary to the nucleotide sequence comprising at least one CpG site that is present in the range from positions 1 to 156 of SEQ ID NO: 1, in the nucleotide sequence of a complementary strand of the CD31 promoter in sample DNA, the below-described primer set (I) is preferable. However, in this case, (F11) to (F14) in the primer set (I) function as a reverse primer, and (R11) to (R14) function as a forward primer.

The primer set (I) is a combination of:

a forward primer comprising a polynucleotide selected from the group consisting of (F11) a polynucleotide consisting of a consecutive partial nucleotide sequence of 10 or more nucleotides, preferably 13 to 23 nucleotides, which is comprised in a region from positions 1 to 108, preferably a region from positions 55 to 82, in the nucleotide sequence shown in SEQ ID NO: 1, and most preferably, a nucleotide sequence consisting of the nucleotide sequence shown in SEQ ID NO: 2, (F12) a polynucleotide capable of hybridizing under stringent conditions with a complementary strand of the polynucleotide of (F11), (F13) a polynucleotide consisting of a nucleotide sequence having a sequence identity of 85% or more with the nucleotide sequence of the polynucleotide of (F11), and (F14) a polynucleotide consisting of a nucleotide sequence comprising a substitution, deletion, insertion and/or addition of one or more nucleotides, with respect to the nucleotide sequence of the polynucleotide of (F11), (F12) or (F13); and a reverse primer comprising a polynucleotide selected from the group consisting of (R11) a polynucleotide consisting of a consecutive partial nucleotide sequence of 10 or more nucleotides, preferably 13 to 23 nucleotides, which is comprised in a complementary nucleotide sequence of a region from positions 109 to 156, preferably a region from positions 121 to 149, in the nucleotide sequence shown in SEQ ID NO: 1, and most preferably, a nucleotide sequence consisting of the nucleotide sequence shown in SEQ ID NO: 3, (R12) a polynucleotide capable of hybridizing under stringent conditions with a complementary strand of the polynucleotide of (R11), (R13) a polynucleotide consisting of a nucleotide sequence having a sequence identity of 85% or more with the nucleotide sequence of the polynucleotide of (R11), and (R14) a polynucleotide consisting of a nucleotide sequence comprising a substitution, deletion, insertion and/or addition of one or more nucleotides, with respect to the nucleotide sequence of the polynucleotide of (R11), (R12) or (R13).

For example, as a primer set for amplifying a nucleotide sequence comprising at least one CpG site that is present in the range from positions 109 to 199, preferably from positions 111 to 199 of SEQ ID NO: 1, in the nucleotide sequence of CD31 promoter in sample DNA, the below-described primer set (II) is preferable.

In addition, also as a primer set for amplifying a nucleotide sequence complementary to the nucleotide sequence comprising at least one CpG site that is present in the range from positions 109 to 199, preferably from positions 111 to 199 of SEQ ID NO: 1, in the nucleotide sequence of a complementary strand of the CD31 promoter in sample DNA, the below-described primer set (II) is preferable. However, in this case, (F21) to (F24) in the primer set (II) function as a reverse primer, and (R21) to (R24) function as a forward primer.

The primer set (II) is a combination of:
a forward primer comprising a polynucleotide selected from the group consisting of (F21) a polynucleotide consisting of a consecutive partial nucleotide sequence of 10 or more nucleotides, preferably 13 to 23 nucleotides, which is comprised in a region from positions 109 to 156, preferably a region from positions 118 to 145, in the nucleotide sequence shown in SEQ ID NO: 1, and most preferably, a nucleotide sequence consisting of the nucleotide sequence shown in SEQ ID NO: 4, (F22) a polynucleotide capable of hybridizing under stringent conditions with a complementary strand of the polynucleotide of (F21), (F23) a polynucleotide consisting of a nucleotide sequence having a sequence identity of 85% or more with the nucleotide sequence of the polynucleotide of (F21), and (F24) a polynucleotide consisting of a nucleotide sequence comprising a substitution, deletion, insertion and/or addition of one or more nucleotides, with respect to the nucleotide sequence of the polynucleotide of (F21), (F22) or (F23); and a reverse primer comprising a polynucleotide selected from the group consisting of (R21) a polynucleotide consisting of a consecutive partial nucleotide sequence of 10 or more nucleotides, preferably 13 to 23 nucleotides, which is comprised in a complementary nucleotide sequence of a region from positions 157 to 199, preferably a region from positions 173 to 199, in the nucleotide sequence shown in SEQ ID NO: 1, and most preferably, a nucleotide sequence consisting of the nucleotide sequence shown in SEQ ID NO: 5, (R22) a polynucleotide capable of hybridizing under stringent conditions with a complementary strand of the polynucleotide of (R21), (R23) a polynucleotide consisting of a nucleotide sequence having a sequence identity of 85% or more with the nucleotide sequence of the polynucleotide of (R21), and (R24) a polynucleotide consisting of a nucleotide sequence comprising a substitution, deletion, insertion and/or addition of one or more nucleotides, with respect to the nucleotide sequence of the polynucleotide of (R21), (R22) or (R23).

For example, as a primer set for amplifying a nucleotide sequence comprising at least one CpG site that is present in the range from positions 157 to 217, preferably from positions 159 to 217 of SEQ ID NO: 1, in the nucleotide sequence of CD31 promoter in sample DNA, the below-described primer set (III) is preferable.

In addition, also as a primer set for amplifying a nucleotide sequence complementary to the nucleotide sequence comprising at least one CpG site that is present in the range from positions 157 to 217, preferably from positions 159 to 217 of SEQ ID NO: 1, in the nucleotide sequence of a complementary strand of the CD31 promoter in sample DNA, the below-described primer set (III) is preferable. However, in this case, (F31) to (F34) in the primer set (III) function as a reverse primer, and (R31) to (R34) function as a forward primer.

The primer set (III) is a combination of:
a forward primer comprising a polynucleotide selected from the group consisting of (F31) a polynucleotide consisting of a consecutive partial nucleotide sequence of 10 or more nucleotides, preferably 12 to 22 nucleotides, which is comprised in a region from positions 157 to 199, preferably a region from positions 160 to 186, in the nucleotide sequence shown in SEQ ID NO: 1, and most preferably, a nucleotide sequence consisting of the nucleotide sequence shown in SEQ ID NO: 6, (F32) a polynucleotide capable of hybridizing under stringent conditions with a complementary strand of the polynucleotide of (F31), (F33) a polynucleotide consisting of a nucleotide sequence having a sequence identity of 85% or more with the nucleotide sequence of the polynucleotide of (F31), and (F34) a polynucleotide consisting of a nucleotide sequence comprising a substitution, deletion, insertion and/or addition of one or more nucleotides, with respect to the nucleotide sequence of the polynucleotide of (F31), (F32) or (F33); and a reverse primer comprising a polynucleotide selected from the group consisting of (R31) a polynucleotide consisting of a consecutive partial nucleotide sequence of 10 or more nucleotides, preferably 16 or less nucleotides, which is comprised in a complementary nucleotide sequence of a region from positions 200 to 217, preferably a region from positions 203 to 217, in the nucleotide sequence shown in SEQ ID NO: 1, and most preferably, a nucleotide sequence consisting of the nucleotide sequence shown in SEQ ID NO: 7, (R32) a polynucleotide capable of hybridizing under stringent conditions with a complementary strand of the polynucleotide of (R31), (R33) a polynucleotide consisting of a nucleotide sequence having a sequence identity of 85% or more with the nucleotide sequence of the polynucleotide of (R31), and (R34) a polynucleotide consisting of a nucleotide sequence comprising a substitution, deletion, insertion and/or addition of one or more nucleotides, with respect to the nucleotide sequence of the polynucleotide of (R31), (R32) or (R33).

For example, as a primer set for amplifying a nucleotide sequence comprising at least one CpG site that is present in the range from positions 200 to 386, preferably from positions 202 to 386 of SEQ ID NO: 1, in the nucleotide sequence of CD31 promoter in sample DNA, the below-described primer set (IV) is preferable.

In addition, also as a primer set for amplifying a nucleotide sequence complementary to the nucleotide sequence comprising at least one CpG site that is present in the range from positions 200 to 386, preferably from positions 202 to 386 of SEQ ID NO: 1, in the nucleotide sequence of a complementary strand of the CD31 promoter in sample DNA, the below-described primer set (IV) is preferable. However, in this case, (F41) to (F44) in the primer set (IV) function as a reverse primer, and (R41) to (R44) function as a forward primer.

The primer set (IV) is a combination of:
a forward primer comprising a polynucleotide selected from the group consisting of
(F41) a polynucleotide consisting of a consecutive partial nucleotide sequence of 10 or more nucleotides, preferably 16 or less nucleotides, which is comprised in a region from positions 200 to 217, preferably a region from positions 203 to 217, in the nucleotide sequence shown in SEQ ID NO: 1, and most preferably, a nucleotide sequence consisting of the nucleotide sequence shown in SEQ ID NO: 8,
(F42) a polynucleotide capable of hybridizing under stringent conditions with a complementary strand of the polynucleotide of (F41),
(F43) a polynucleotide consisting of a nucleotide sequence having a sequence identity of 85% or more with the nucleotide sequence of the polynucleotide of (F41), and
(F44) a polynucleotide consisting of a nucleotide sequence comprising a substitution, deletion, insertion and/or addition of one or more nucleotides, with respect to the nucleotide sequence of the polynucleotide of (F41), (F42) or (F43); and
a reverse primer comprising a polynucleotide selected from the group consisting of
(R41) a polynucleotide consisting of a consecutive partial nucleotide sequence of 10 or more nucleotides, preferably 13 to 23 nucleotides, which is comprised in a complementary nucleotide sequence of a region from positions 218 to 386, preferably a region from positions 260 to 287, in the nucleotide sequence shown in SEQ ID NO: 1, and most preferably, a nucleotide sequence consisting of the nucleotide sequence shown in SEQ ID NO: 9,
(R42) a polynucleotide capable of hybridizing under stringent conditions with a complementary strand of the polynucleotide of (R41),
(R43) a polynucleotide consisting of a nucleotide sequence having a sequence identity of 85% or more with the nucleotide sequence of the polynucleotide of (R41), and
(R44) a polynucleotide consisting of a nucleotide sequence comprising a substitution, deletion, insertion and/or addition of one or more nucleotides, with respect to the nucleotide sequence of the polynucleotide of (R41), (R42) or (R43).

With regard to the polynucleotides described in the above (F12), (R12), (F22), (R22), (F32), (R32), (F42) and (R42), the term "stringent conditions" means conditions under which, what is called, a specific hybrid is formed, and a non-specific hybrid is not formed. Such stringent conditions can be determined, as appropriate, with reference to, for example, Green and Sambrook, Molecular Cloning, 4th Ed (2012), Cold Spring Harbor Laboratory Press. Specifically, such stringent conditions can be determined based on the temperature applied upon Southern hybridization or the concentration of salts contained in the solution, and the temperature applied upon the washing step in Southern hybridization or the concentration of salts contained in the solution. More specifically, for example, in a hybridization step, stringent conditions consist of a sodium concentration of 25 to 500 mM, preferably 25 to 300 mM, and a temperature of 40° C. to 68° C., preferably 40° C. to 65° C. Further specifically, hybridization can be carried out in 1 to 7×SSC and 0.02% to 3% SDS, and at a temperature of 40° C. to 60° C. Moreover, a washing step may be carried out after completion of the hybridization, and the washing step can be carried out, for example, in 0.1 to 2×SSC and 0.1% to 0.3% SDS, and at a temperature of 50° C. to 65° C.

With regard to the polynucleotides described in the above (F13), (R13), (F23), (R23), (F33), (R33), (F43) and (R43), the identity value indicates a value calculated with default settings, using software for calculating an identity among a plurality of nucleotide sequences (e.g., FASTA, DANASYS, and BLAST). The identity value between nucleotide sequences is obtained by calculating the number of matched nucleotides when a pair of nucleotide sequences are aligned to obtain the maximum matching rate and then measuring the rate of the number of the matched nucleotides to the total number of nucleotides in the compared nucleotide sequence. Herein, when there is a gap, the aforementioned total number of nucleotides means the number of nucleotides, in which one cap is counted as one nucleotide. For details of the method of determining identity, please refer to, for example, Altschul et al, Nuc. Acids. Res. 25, 3389-3402, 1977 and Altschul et al, J. Mol. Biol. 215, 403-410, 1990. In the polynucleotides described in the above (F13), (R13), (F23), (R23), (F33), (R33), (F43) and (R43), the sequence identity values each independently are more preferably 90% or more, even more preferably 95% or more, and further preferably 98% or more.

With regard to the polynucleotides described in the above (F14), (R14), (F24), (R24), (F34), (R34), (F44) and (R44), the term "one or more" means preferably 1 to 5, more preferably 1 to 4, further preferably 1 to 3, particularly preferably 1 or 2, and most preferably 1. Further preferably, a substitution, deletion, insertion and/or addition of one or more nucleotides take place only at the 5'-terminus of the nucleotide sequence of a certain polynucleotide.

<Method for Producing Mesenchymal Stem Cell-Containing Formulation>

The present invention also provides, as another embodiment,
a method for producing a mesenchymal stem cell-containing formulation from a sample containing cells, said method comprising:
a sample selection step of detecting a nucleotide sequence comprising at least one CpG site that has been methylated at a higher percentage in mesenchymal stem cells than in other cells, in the nucleotide sequence of CD31 promoter or a complementary strand thereof, comprised in genomic DNA obtained from the sample, and then selecting the sample to be used in the production of the formulation based on the detection results; and
a formulation production step of producing the formulation from the selected sample.

Individual materials used, and a method of detecting a nucleotide sequence comprising at least one of the above-described CpG sites in genomic DNA in the sample selection step, are the same as those described in the nucleic acid detection step.

In the sample selection step, a sample to be used in the production of the aforementioned formulation is further selected based on the detection results of a nucleotide sequence comprising at least one of the above-described CpG sites. Since the detection results reflect the content of mesenchymal stem cells in the sample, the results are useful as an indicator for selecting a sample suitable for the production of a mesenchymal stem cell-containing formulation. In particular, in this step, it is preferable to selectively detect the amount of DNA comprising a nucleotide sequence containing the methylated CpG site, in a nucleotide sequence comprising at least one of the above-described CpG sites in CD31 promoter or a complementary strand thereof, or the amount of DNA comprising a nucleotide sequence containing the unmethylated CpG site. In the sample selection step, using these detection results as an indicator, a sample containing large quantities of mesenchymal stem cells is selected, and the selected sample can be used in the production of the formulation. Also in this case, as described in detail in the above section "Method for evaluating the content of mesenchymal stem cells," a sample may be selected using the detection results themselves as an indicator, without obtaining the content of mesenchymal stem cells, or the content of mesenchymal stem cells may be obtained from the detection results based on the correlation of the detection results with the content of mesenchymal stem cells, and the thus obtained content of mesenchymal stem cells may be used as an indicator to select a sample.

The formulation production step is a step of producing the above-described formulation from the sample selected in the sample selection step. The formulation production step is not particularly limited, and this step may include, for example, a step of further separating, culturing, concentrating, and/or recovering mesenchymal stem cells from the selected sample, a step of combining the mesenchymal stem cells obtained by separation, culture, concentration, and/or recovery from the sample, with other components of a formulation, as described in the after-mentioned <Other components comprised in mesenchymal stem cell-containing formulation>, and the like. The above-described formulation production steps each select a preferred means depending on purpose, and further, individual steps can be combined with one another, as appropriate, if necessary. The formulation production steps will be each described in detail below.

The separation step is not particularly limited, as long as it is a step capable of separating a sample containing mesenchymal stem cells. Such a sample containing mesenchymal stem cells can be separated, for example, by a known method such as centrifugation, filtration through a mesh, a filter, etc., or a known separation method using a hollow fiber separation membrane.

The culture step is not particularly limited, as long as it is a step capable of culturing the sample obtained by the above-described separation step and/or a sample before subjecting the separation step. In particular, in an aspect of culturing the sample obtained by the separation step, high-purity mesenchymal stem cells can be produced. The culture method is not particularly limited, and an appropriate known culture method can be selected, depending on purpose.

The concentration step is not particularly limited, as long as it is a step of, for example, concentrating the sample obtained by the above-described separation and/or culture steps, to increase the concentration of mesenchymal stem cells to a concentration suitable for the treatment. As such a concentration method, the sample can be concentrated by a known method such as centrifugation, filtration through a mesh or a filter, or a known separation method using a hollow fiber separation membrane.

The recovery step is not particularly limited, as long as it is, for example, a step of removing contaminants, wastes, culture components, etc., from the sample obtained by the above-described separation, culture and/or concentration steps, so as to produce high-purity mesenchymal stem cells. As such a recovery method, mesenchymal stem cells can be recovered from the above-described sample, for example, according to a known method, such as centrifugation, filtration through a mesh or a filter, or a known separation method using a hollow fiber separation membrane.

A combination of individual formulation production steps described above is not particularly limited, and the order of carrying out the steps is not particularly limited, either. As a combination of individual steps, for example, all of the above-described separation, culture, concentration, and recovery steps may be carried out, or from the above-described individual formulation production steps, steps such as separation, culture and concentration, or separation, culture and recovery, or separation, concentration and recovery, or separation and culture, or separation and concentration, or separation and recovery, or culture and concentration, or culture and recovery, can be appropriately selected, and the selected steps can be then carried out. Otherwise, as such a formulation production step, only the separation step can be carried out.

The mesenchymal stem cells obtained by the above-described separation, culture, concentration and/or recovery are combined with other components for a formulation, as described in the after-mentioned <Other components comprised in mesenchymal stem cell-containing formulation>, so that a mesenchymal stem cell-containing formulation may be produced.

Specific examples of the formulation production step include a step of separating SVF containing mesenchymal stem cells from adipose tissues and then producing a mesenchymal stem cell-containing formulation from the SVF, and a step of separating SVF containing mesenchymal stem cells from adipose tissues, then culturing the SVF to produce a high-purity mesenchymal stem cells, and then producing a mesenchymal stem cell-containing formulation from the obtained mesenchymal stem cells.

Moreover, the formulation production step of the present invention can comprise a step of cryopreserving a sample containing mesenchymal stem cells. In this aspect in which the formulation production step includes a step of cryopreserving the above-described sample, after the sample has been thawed, it is subjected to separation, culture, concentration and/or recovery, as necessary, and thereafter, a mesenchymal stem cell-containing formulation may be produced from the obtained mesenchymal stem cells. Alternatively, after the above-described sample has been thawed, it may be diluted with an infusion formation or the like, as necessary, to produce a mesenchymal stem cell-containing formulation, or the sample is combined with other components for a formulation, as described in the after-mentioned <Other components comprised in mesenchymal stem cell-containing formulation>, so that a mesenchymal stem cell-containing formulation may be produced.

The infusion formulation is not particularly limited in the present description, as long as it is a solution used upon the treatment of a human. Examples of the infusion formulation include a normal saline, a 5% glucose solution, a Ringer solution, a lactated Ringer solution, an acetated Ringer solution, a starting solution (No. 1 solution), a dehydration replenishing solution (No. 2 solution), a maintenance infusion (No. 3 solution), and a postoperative recovery solution (No. 4 solution).

<Other Components Comprised in Mesenchymal Stem Cell-Containing Formulation>

The mesenchymal stem cell-containing formulation is not particularly limited, as long as it is a formulation containing mesenchymal stem cells, which has a form that can be used for a desired purpose such as regenerative medicine. Thus, the mesenchymal stem cell-containing formulation may comprise other components, such as a liquid or solid cell culture medium, albumin or serum, a liquid or solid carrier, an amino acid, a vitamin, a buffer, a thickener, a normal saline, a cryopreservation solution, water, and further cells, as well as mesenchymal stem cells. Examples of further cells include pluripotent stem cells such as iPS cells or ES cells, and organ cells such as endothelial cells, wall cells, myoblasts, myocardial cells, liver cells, endocrine progenitor cells, nerve cells, pancreatic 13 cells, or mature adipocytes. A mesenchymal stem cell-containing formulation comprising mesenchymal stem cells and such further cells can be used for administration to a subject or reconstruction of tissues or organs in vitro.

<Form of Mesenchymal Stem Cell-Containing Formulation>

The form of the mesenchymal stem cell-containing formulation is not particularly limited. Examples of the form of the mesenchymal stem cell-containing formulation include liquid agents such as an injection, a suspension agent, a solution agent or a spray agent, sheet formulations, and gel formulations. The mesenchymal stem cell-containing formulation having the aforementioned form is easily administered to a subject.

The usage of the mesenchymal stem cell-containing formulation is not limited. The mesenchymal stem cell-containing formulation can be utilized, for example, for direct administration to a subject; or the mesenchymal stem cells can be mixed with further cells, so that the obtained mixture can be utilized as a supply source of mesenchymal stem cells for production of a cell-containing composition; or the mesenchymal stem cell-containing formulation can be utilized as a supply source of cells for reconstruction of tissues or organs, which is carried out in vitro.

Specific intended use of the mesenchymal stem cell-containing formulation in the case of using the formulation by being administered to a subject such as a human will be described in the section <Therapeutic method using mesenchymal stem cells> below.

<Kit>

The present invention also provides, as another embodiment, a kit for evaluating the content of mesenchymal stem cells in a sample containing cells, said kit comprising a primer set capable of amplifying a region comprising any one or more selected from: a CpG site consisting of C at position 109 and G at position 110, a CpG site consisting of C at position 157 and G at position 158, a CpG site consisting of C at position 200 and G at position 201, and a CpG site consisting of C at position 218 and G at position 219, in the nucleotide sequence of CD31 promoter shown in SEQ ID NO: 1; and a CpG site complementary to the CpG site consisting of C at position 109 and G at position 110 in the nucleotide sequence of SEQ ID NO: 1, a CpG site complementary to the CpG site consisting of C at position 157 and G at position 158 in the nucleotide sequence of SEQ ID NO: 1, a CpG site complementary to the CpG site consisting of C at position 200 and G at position 201 in the nucleotide sequence of SEQ ID NO: 1, and a CpG site complementary to the CpG site consisting of C at position 218 and G at position 219 in the nucleotide sequence of SEQ ID NO: 1, in a nucleotide sequence complementary to the nucleotide sequence of CD31 promoter shown in SEQ ID NO: 1.

As a primer set capable of amplifying a region comprising a CpG site consisting of C at position 109 and G at position 110 in the nucleotide sequence of CD31 promoter shown in SEQ ID NO: 1, or a region comprising a CpG site complementary to the aforementioned CpG site in the nucleotide sequence of a complementary strand of the CD31 promoter shown in SEQ ID NO: 1, the above-described primer set (I) is preferable.

As a primer set capable of amplifying a region comprising a CpG site consisting of C at position 157 and G at position 158 in the nucleotide sequence of CD31 promoter shown in SEQ ID NO: 1, or a region comprising a CpG site complementary to the aforementioned CpG site in the nucleotide sequence of a complementary strand of the CD31 promoter shown in SEQ ID NO: 1, the above-described primer set (II) is preferable.

As a primer set capable of amplifying a region comprising a CpG site consisting of C at position 200 and G at position 201 in the nucleotide sequence of CD31 promoter shown in SEQ ID NO: 1, or a region comprising a CpG site complementary to the aforementioned CpG site in the nucleotide sequence of a complementary strand of the CD31 promoter shown in SEQ ID NO: 1, the above-described primer set (III) is preferable.

As a primer set capable of amplifying a region comprising a CpG site consisting of C at position 218 and G at position 219 in the nucleotide sequence of CD31 promoter shown in SEQ ID NO: 1, or a region comprising a CpG site complementary to the aforementioned CpG site in the nucleotide sequence of a complementary strand of the CD31 promoter shown in SEQ ID NO: 1, the above-described primer set (IV) is preferable.

When the kit of the present invention is used in selective detection method 1 or 2, it is preferable that the present kit further comprise a restriction enzyme. As such a restriction enzyme, those described in detail regarding selective detection method 1 or 2 are preferable, but are not limited thereto.

When the kit of the present invention is used in selective detection method 3, it is preferable that the present kit further comprise bisulfite and deoxyribonucleotide triphosphate. An example of the bisulfite used herein is sodium bisulfite salt.

It is preferable that the kit of the present invention further comprise various types of reagents used in a nucleic acid amplification reaction, such as polymerase, deoxyribonucleotide triphosphate, and a buffer.

<Therapeutic Method Using Mesenchymal Stem Cells>

The present invention also provides, as another embodiment, a method for treating a subject in need of the treatment of disease or disorder, using mesenchymal stem cells, said method comprising an administration step of administering a mesenchymal stem cell-containing formulation obtained by the method described in detail in the above <Method for producing mesenchymal stem cell-containing formulation>, or mesenchymal stem cells derived from a sample that has been evaluated to comprise mesenchymal stem cells by the method described in detail in the above <Method for evaluating the content of mesenchymal stem cells>, to a subject having disease or disorder.

In the present invention, examples of the disease or disorder that can be a target of a therapeutic method using the above-described mesenchymal stem cell-containing formulation or the above-described mesenchymal stem cells include diseases or disorders such as immune disease, ischemic disease (lower limb ischemia, ischemic heart disease (myocardial infarction, etc.), coronary heart disease, cerebrovascular ischemia, kidney ischemia, lung ischemia, etc.), neurological disease, Crohn's disease, graft versus host disease (GVHD), inflammatory bowel disease including ulcerative colitis, collagen disease including systemic lupus erythematosus, cirrhosis of the liver, cerebral infarction, intracerebral hematoma, cerebral vasospasm, radiation enteritis, atopic dermatitis, multiple sclerosis, rheumatoid arthritis, psoriasis, lupus erythematosus, diabetes, mycosis fungoides (Alibert-Bazin syndrome), scleroderma, disease caused by degeneration and/or inflammation of connective tissues such as cartilage, eye disease, angiogenesis-related disease, congestive heart failure, cardiomyopathy, wound, epithelial damage, fibrosis, lung disease, and cancer. In addition, the therapeutic method using the above-described mesenchymal stem cell-containing formulation or the above-described mesenchymal stem cells also includes administering the above-described mesenchymal stem cell-containing formulation or mesenchymal stem cells derived from the above-described sample to a subject in need of regeneration of the heart muscle, generation of myocardial cells, angiogenesis, repair of blood vessel, or suppression of immune response, so as to achieve regeneration of the heart muscle, generation of myocardial cells, angiogenesis, repair of blood vessel, or suppression of immune response in the above-described subject. Moreover, in the present invention, the therapeutic method using the above-described mesenchymal stem cell-containing formulation or the above-described mesenchymal stem cells also includes a treatment, operation or improvement for cosmetic purpose. Such cosmetic purpose not only includes a cosmetic treatment performed on a subject under totally healthy conditions, but also includes a cosmetic treatment performed on a subject with postoperative or post-traumatic deformation and congenital deformation. For example, the therapeutic method of the present invention can be utilized for breast tissue augmentation surgery (breast enlargement surgery, breast reconstruction), tissue augmentation surgery for subsidence occurring at the cheek or the upper and lower eyelids, and tissue augmentation surgery for facial hemiatrophy, face or funnel chest. However, the disease or disorder that can be the target of the present invention is not limited thereto.

With regard to other examples of the diseases or disorders of subjects, which can be treated using the above-described mesenchymal stem cell-containing formulation or the above-described mesenchymal stem cells, further specific examples of the above-described diseases or disorders, and specific therapeutic procedures, the matters described in the following publications can be referred to: Hare et al., J. Am. Coll. Cardiol., 2009 December 8; 54(24): 2277-2286, Honmou et al., Brain 2011: 134; 1790-1807, Makhoul et al., Ann. Thorac. Surg. 2013; 95: 1827-1833, Japanese Patent No. 590577, JP Patent Publication (Kokai) No. 2010-518096 A, JP Patent Publication (Kohyo) No. 2012-509087 A, JP Patent Publication (Kohyo) No. 2014-501249 A, JP Patent Publication (Kokai) No. 2013-256515 A, JP Patent Publication (Kokai) No. 2014-185173 A, JP Patent Publication (Kohyo) No. 2010-535715 A, JP Patent Publication (Kokai) No. 2015-038059 A, JP Patent Publication (Kokai) No. 2015-110659 A, JP Patent Publication (Kohyo) No. 2006-521121 A, JP Patent Publication (Kohyo) No. 2009-542727 A, JP Patent Publication (Kokai) No. 2014-224117 A, JP Patent Publication (Kokai) No. 2015-061862 A, JP Patent Publication (Kohyo) No. 2002-511094 A, JP Patent Publication (Kohyo) No. 2004-507454 A, JP Patent Publication (Kohyo) No. 2010-505764 A, JP Patent Publication (Kohyo) No. 2011-514901 A, JP Patent Publication (Kokai) No. 2013-064003 A, JP Patent Publication (Kokai) No. 2015-131795 A, etc.

Furthermore, in the present invention, examples of the disease or disorder that can be the target of the therapeutic method using the above-described mesenchymal stem cell-containing formulation or the above-described mesenchymal stem cells do not only include diseases or disorders that can be treated, dealt with, or improved by only mesenchymal stem cells, but also include diseases or disorders that can be treated, dealt with, or improved by a combination of mesenchymal stem cells with further other cells. For example, since mesenchymal stem cells have an angiogenic action or an action to promote fixation of tissues, regeneration of the tissue or organ of a subject is promoted by administration of a cell-containing composition comprising pluripotent stem cells such as iPS cells or ES cells and/or organ cells such as mature adipocytes, mesenchymal stem cells, and as necessary, vascular endothelial cells, and thereby, the disease or disorder of the subject can be treated, dealt with, or improved. Besides, the aforementioned cell-containing composition can be produced with reference to the mixing ratio described in a laid-open publication (WO2013/047639) of Public University Corporation, Yokohama City University.

Further, administration of adipose tissues comprising mesenchymal stem cells or a cell-containing composition comprising mesenchymal stem cells and mature adipose tissues to a subject is effective for breast enlargement surgery or breast reconstruction performed on the subject. This method is called CAL (Cell Assisted Lipo-transfer) method. With regard to the specific method of breast enlargement surgery or breast reconstruction, such breast enlargement surgery or breast reconstruction may be carried out in accordance with the method described in a laid-open publication (JP Patent Publication (Kokai) No. 2008-271971 A) of Biomaster Inc.

In the administration step, the above-described mesenchymal stem cell-containing formulation or mesenchymal stem cells derived from the above-described sample are administered to a subject having the above-described disease or disorder. In the present invention, the term "administration" includes "transplantation." At this time, the "mesenchymal stem cell-containing formulation" to be administered can be produced from the above-described sample by the method described in the above <Method for producing mesenchymal stem cell-containing formulation>. In addition, the administered "mesenchymal stem cells derived from the above-described sample" may be the above-described sample itself containing mesenchymal stem cells, or mesenchymal stem cells separated from the above-described sample, or mesenchymal stem cells cultured after being separated from the above-described sample. The above-described mesenchymal stem cell-containing formulation or the above-described mesenchymal cells can be derived from an animal having the same species as a subject to be administered therewith, or the same individual as the subject, but are not limited thereto.

In the administration step, the appropriate dose of the mesenchymal stem cells to be administered to a subject or the number of administrations thereof can be determined in advance, by evaluating the content of mesenchymal stem cells in a sample containing cells. The content of mesenchymal stem cells in the above-described sample is not clear, if the content of mesenchymal stem cells has not been evaluated. Accordingly, when mesenchymal stem cells derived from the above-described sample are administered to a subject without evaluating the content of mesenchymal stem cells, the appropriate dose of the mesenchymal stem cells or the number of administrations thereof would not be grasped in advance. Thus, the procedure of confirming the effects of the mesenchymal stem cells after the administration thereof and then administering the cells again, would be necessary. As a result, it would be likely that the dose of the mesenchymal stem cells or the number of administrations thereof unnecessarily increases, and that burden on the subject also increases. In the present invention, since the appropriate dose of the mesenchymal stem cells or the number of administrations thereof applied in the administration step can be determined based on the content of mesenchymal stem cells in the above-described sample that has been evaluated in the step of evaluating the content of mesenchymal stem cells in a sample containing cells, the time and labor of administration, costs, burden on a subject, etc. can be reduced.

The method of administering a mesenchymal stem cell-containing formulation or mesenchymal stem cells derived from the above-described sample to a subject is not particularly limited. Examples of the administration method include subcutaneous injection, lymph node injection, intravenous injection, intraperitoneal injection, intrathoracic injection, direction injection into a local site, and direct transplantation into affected area, but are not limited thereto.

The subject is typically a human, but it may also be another animal. Examples of such another animal include mammals such as a dog, a cat, a bovine, a horse, a swine, sheep, a monkey or a ferret, and birds such as a chicken.

First Preferred Embodiment of the Present Invention

A first preferred embodiment of the present invention relates to
a method of transplanting an adipose tissue into a human, which comprises:
at least one step selected from a step 101 of evaluating the content of human adipose tissue-derived mesenchymal stem cells (ASCs) in a human adipose tissue-derived stromal vascular fraction (SVF) and a step 101' of evaluating the content of human adipose tissue-derived mesenchymal stem cells (ASCs) in a tissue comprising mature adipocytes;
a step 102 of combining the SVF with the tissue comprising mature adipocytes, to produce an adipose tissue for transplantation; and
a step 103 of transplanting the adipose tissue for transplantation into a human, wherein
the step 101 comprises a nucleic acid detection step of detecting a nucleotide sequence comprising at least one of a CpG site consisting of C at position 157 and G at position 158 of SEQ ID NO: 1, and a CpG site complementary to the CpG site consisting of C at position 157 and G at position 158 of SEQ ID NO: 1 in a nucleotide sequence complementary to the nucleotide sequence of SEQ ID NO: 1 comprised in genomic DNA obtained from the SVF, and
the step 101' comprises a nucleic acid detection step of detecting a nucleotide sequence comprising at least one of a CpG site consisting of C at position 157 and G at position 158 of SEQ ID NO: 1, and a CpG site complementary to the CpG site consisting of C at position 157 and G at position 158 of SEQ ID NO: 1 in a nucleotide sequence complementary to the nucleotide sequence of SEQ ID NO: 1 comprised in genomic DNA obtained from the tissue comprising mature adipocytes.

SVF (stromal vascular fraction) is a cell population derived from an adipose tissue, and it is obtained by treating an adipose tissue with an enzyme and then centrifuging them.

When the first preferred embodiment of the present invention comprises the step 101, the amount of ASCs can be quantified with good precision, in SVF that is a cell population comprising human adipose tissue-derived mesenchymal stem cells (ASCs) in a state in which the ASCs co-exist with other cells derived from an adipose tissue.

When the first preferred embodiment of the present invention comprises the step 101, by grasping the amount of ASCs in SVF according to the step 101, it is possible to evaluate whether or not the SVF is suitable for transplantation, and to determine the amount of the SVF to be combined with a tissue comprising mature adipocytes in the step 102. When the first preferred embodiment of the present invention comprises the step 101, the step 102 may comprise combining the SVF in an amount corresponding to the amount of ASCs to be added, with the tissue comprising mature adipocytes.

When the first preferred embodiment of the present invention comprises the step 101', by grasping the amount of ASCs in the tissue comprising mature adipocytes according to the step 101', it is possible to evaluate whether or not the tissue is suitable for transplantation, and to determine the amount of the SVF to be combined with the tissue in the step 102.

The step 101 and/or the step 101' of the first preferred embodiment of the present invention can directly quantify the amount of ASCs in an adipose tissue by extracting genomic DNA from the tissue using a commercially available kit, without necessity of separating cells through an enzymatic treatment, such as a collagenase treatment, of the tissue. Accordingly, the step 101 and/or the step 101' are much simpler than a flow cytometry (FACS), which requires separating cells before measurement. Furthermore, the step 101 and/or the step 101' can quantify the amount of ASCs in the SVF or in the tissue, even in a cell amount of approximately one hundreds (1/100) ($10^3$ to $10^4$ cells) in comparison to the flow cytometry (FACS) for measuring a cell count.

In the step 101 and/or the step 101' of the first preferred embodiment of the present invention, unlike FACS, in which one instrument can analyze only one sample at a time, it is possible to analyzes a plurality of samples at a time (for example, the step 101 and/or the step 101' can simultaneously analyze 18 samples for quantifying 6 specimens at N=3). As such, according to the method of the first preferred embodiment of the present invention, it is possible to cope with the case of simultaneously transplanting an adipose tissue into multiple subjects.

Preferably, the method of the first preferred embodiment of the present invention further comprises, before the step 102, a step 104 of culturing the above-described SVF to be used in the step 102. When the first preferred embodiment of the present invention comprises the step 101, the step 104 may be carried out before and/or after the step 101. By subjecting the SVF to an adhesion culture, the percentage of ASCs can be enhanced. In the present invention, a cell population, in which SVF is cultured to enhance the percentage of ASCs, is also included in the scope of SVF. A cell population in which the percentage of ASCs has been enhanced, obtained by culturing SVF in the step 104, may be added to the tissue comprising mature adipocytes. Such addition increases the percentage of ASCs in the tissue and, as a result of which the survival percentage of the tissue transplanted in the step 103 is enhanced.

More preferably, the method of the first preferred embodiment of the present invention comprises both of the step 101 and the step 101'; and further preferably, the method of the first preferred embodiment of the present invention further comprises, before the step 102, a step 105 of determining the amount ratio between the above-described SVF and the above-described tissue comprising mature adipocytes, which are to be combined in the step 102, based on the results of the step 101 and the results of the step 101'.

More preferably, the method of the first preferred embodiment of the present invention comprises, after the step 103, a step 106 of combining second SVF derived from a human adipose tissue with a second tissue comprising mature adipocytes to produce a second adipose tissue for transplantation, and a step 107 of transplanting the second adipose tissue for transplantation into a human, and the present method further preferably comprises a step 108 of predicting the amount of the second SVF and the amount of a human adipose tissue necessary for preparation of the second SVF, based on the results of the step 101 and/or the step 101'. Transplanting the adipose tissues multiple times is advantageous in that it can provide a sufficient amount of the adipose tissue to the patient in a breast enlargement surgery, a breast reconstruction or the like. This embodiment may be helpful in precisely predicting the amount of SVF or the amount of highly purified mesenchymal stem cells obtainable from an adipose tissue. Using such predicted amounts, conditions for obtaining SVF or highly purified mesenchymal stem cells from the adipose tissue (e.g., culture conditions, etc.) can be easily determined.

The first preferred embodiment of the present invention comprising the step 106 and the step 107 may further comprise a step 104 of culturing at least a part of the SVF before and/or after the step 102. In this embodiment, the second SVF (including the second and subsequent SVFs) may be the SVF obtained by culturing of the step 104. In an embodiment in which the SVF obtained by culturing of the step 104 is used as the second SVF in the step 106, an adipose tissue for preparing the second SVF is not necessary, and the second and subsequent transplantations need to extract smaller amount of adipose tissues from the patient. As such, this embodiment would impose less burden on the patient, from whom the adipose tissues are derived, and be less invasive for the patient.

Second Preferred Embodiment of the Present Invention

A second preferred embodiment of the present invention relates to a method of culturing a human adipose tissue-derived stromal vascular fraction (SVF), which comprises:

a step 201 of evaluating the content of human adipose tissue-derived mesenchymal stem cells (ASCs) in SVF derived from a human adipose tissue;

a step 202 of determining conditions for culturing the SVF, based on the results of the step 201; and a step 203 of culturing the SVF under the conditions determined in the step 202, wherein the step 201 comprises a nucleic acid detection step of detecting a nucleotide sequence comprising at least one of a CpG site consisting of C at position 157 and G at position 158 of SEQ ID NO: 1, and a CpG site complementary to the CpG site consisting of C at position 157 and G at position 158 of SEQ ID NO: 1 in a nucleotide sequence complementary to the nucleotide sequence of SEQ ID NO: 1 comprised in genomic DNA obtained from the SVF.

According to the method of the second preferred embodiment of the present invention, the amount of ASCs contained in the SVF is evaluated in the step 201; then, in the step 202, conditions for culturing the SVF, such as a culture time and the number of subcultures, are determined based on the results of the step 201 (information such as the amount of ASCs or the amount of cells other than the ASCs, etc.); and then, in the step 203, the SVF is cultured under the conditions determined in the step 202. The SVF obtained after completion of the culture in the step 203 can be used as SVF in the step 101 or the step 102 of the first preferred embodiment of the present invention.

Third Preferred Embodiment of the Present Invention

A third preferred embodiment of the present invention relates to a method of evaluating the content of human adipose tissue-derived mesenchymal stem cells (ASCs) or the content of cells other than the ASCs in a human adipose tissue-derived stromal vascular fraction (SVF), wherein the method comprises a nucleic acid detection step of detecting a nucleotide sequence comprising at least one of a CpG site consisting of C at position 157 and G at position 158 of SEQ ID NO: 1, and a CpG site complementary to the CpG site consisting of C at position 157 and G at position 158 of SEQ ID NO: 1 in a nucleotide sequence complementary to the nucleotide sequence of SEQ ID NO: 1 comprised in genomic DNA obtained from the SVF.

According to the method of the third preferred embodiment of the present invention, the content of ASCs, or the content of cells other than the ASCs (e.g., the total content of vascular endothelial cells, pericytes, and blood-derived cells) in the SVF can be evaluated.

In the method of the third preferred embodiment of the present invention, the above-described SVF is preferably subcultured SVF. The subculture of the SVF is carried out to enhance the percentage of ASCs, so as to purify it. According to this embodiment, the amount of cells other than the ASCs, which remain from the initial stage of subculture, or the amount of cells unintentionally differentiated into other cells than ACSs during the subculture, contained in the above-described SVF, can be evaluated.

In the method of the third preferred embodiment of the present invention, the above-described SVF is preferably SVF that has been frozen and then thawed. This embodiment is useful for confirming the quality of the thawed SVF, when the SVF is cryopreserved.

EXAMPLES

FIG. 1 shows a CpG sequence containing methylated cytosine (C) in the DNA nucleotide sequence (SEQ ID NO: 1) of a CD promoter comprised in the genomic DNA of human adipose tissue-derived mesenchymal stem cells (ASCs) with an underlined portion (Stem Cells, 2007, 25(4): 852-61). FIG. 1 also shows CCGG that is a recognition sequence of the methylation-sensitive restriction enzyme HapII and the methylation-non-sensitive restriction enzyme MspI that is an isoschizomer of HapII, with bold letters.

FIG. 1 also shows a position corresponding to each primer consisting of the nucleotide sequence shown in any one of SEQ ID NOS: 2 to 9.

The methylation-dependent restriction enzyme McrBC recognizes DNA comprising a dinucleotide consisting of (A/G)$^m$C and cleaves it. Herein, $^m$C indicates a methylated cytosine. For the cleavage of DNA with McrBC, at least two of the above-described dinucleotides, which are apart from each other by 40 to 3,000 nucleotides on DNA, are necessary.

Herein, a primer set consisting of a forward primer that is an oligonucleotide consisting of the nucleotide sequence shown in SEQ ID NO: 2 and a reverse primer that is an oligonucleotide consisting of the nucleotide sequence shown in SEQ ID NO: 3 is referred to as a first primer set. A region in SEQ ID NO: 1 amplified by PCR using the first primer set, in the DNA nucleotide sequence (SEQ ID NO: 1) of CD31 promoter in human genomic DNA, is referred to as a first region.

In addition, a primer set consisting of a forward primer that is an oligonucleotide consisting of the nucleotide sequence shown in SEQ ID NO: 4 and a reverse primer that is an oligonucleotide consisting of the nucleotide sequence shown in SEQ ID NO: 5 is referred to as a second primer set. A region in SEQ ID NO: 1 amplified by PCR using the second primer set, in the DNA nucleotide sequence (SEQ ID NO: 1) of CD31 promoter in human genomic DNA, is referred to as a second region.

Moreover, a primer set consisting of a forward primer that is an oligonucleotide consisting of the nucleotide sequence shown in SEQ ID NO: 6 and a reverse primer that is an oligonucleotide consisting of the nucleotide sequence shown in SEQ ID NO: 7 is referred to as a third primer set. A region in SEQ ID NO: 1 amplified by PCR using the third primer set, in the DNA nucleotide sequence (SEQ ID NO: 1) of CD31 promoter in human genomic DNA, is referred to as a third region.

Furthermore, a primer set consisting of a forward primer that is an oligonucleotide consisting of the nucleotide sequence shown in SEQ ID NO: 8 and a reverse primer that is an oligonucleotide consisting of the nucleotide sequence shown in SEQ ID NO: 9 is referred to as a fourth primer set. A region in SEQ ID NO: 1 amplified by PCR using the fourth primer set, in the DNA nucleotide sequence (SEQ ID NO: 1) of CD31 promoter in human genomic DNA, is referred to as a fourth region.

Experiment 1

Cultured human-derived ASCs were obtained by the following procedures. Human adipose tissues provided from a volunteer, from whom a consent was obtained, were treated with 0.1% collagenase (Wako Pure Chemical Industries, Ltd., 038-22361) (37° C., 30 minutes), and were then centrifuged (800 g, 5 minutes) to recover cells. The cells were cultured using α-MEM (Life Technologies Japan Ltd., 12561-049)+10% FBS (HyClone, SH30070.03)+1% Antibiotic-Antimycotic (Life Technologies Japan Ltd., 15240-062). After completion of the 3rd subculture (subcultured at the time point of confluency of 80% to 90%), the cells were obtained as cultured human-derived ASCs. Genomic DNA was extracted from the above-described cultured human-derived ASCs according to the following procedures. DNA was extracted using NucleoSpin® Tissue (Takara Bio, Inc., U0952S), and operations were carried out in accordance with protocols included therewith.

The thus extracted DNA sample was used as a template without performing a restriction enzyme treatment, and real-time PCR was carried out using the first primer set under the following conditions. First, pure water was added to 5 μL of template DNA (6.25 ug) and 2 μL of the first primer set (a forward primer and a reverse primer, each 4 pmol) to prepare 10 μL of premix. To this solution, 10 μL of 2×SYBR Premix ExTaq GC (Takara Bio, Inc., RR071A) was added to prepare a reaction solution, and real-time PCR was then carried out using Applied Biosystems 7300 Real Time PCR System (Life Technologies Japan Ltd.). The reaction was carried out under reaction conditions of (1) 95° C., 30 seconds (2) 95° C., 15 seconds, (3) 60° C., 30 seconds, and (4) the operations (2) and (3) that were repeatedly performed 40 times. The Ct value was automatically calculated using 7300 SDS instrument software (Life Technologies Japan Ltd.).

A mean value of the Ct values ($Ct_{total}$) (n=5) obtained under the aforementioned conditions was 23.44. $Ct_{total}$ reflects the total amount of CD31 promoters contained in the genomic DNA of human ASCs ($I_{total}$).

The above extracted DNA sample was treated with the methylation-sensitive restriction enzyme HapII (Takara Bio, Inc., 1053AH), so that a CCGG sequence, in which C had not been methylated, was selectively cleaved. Using the HapII-treated DNA as a template, and also using the first primer set, real-time PCR was carried out under the same conditions as described above. A mean value of the Ct values ($Ct_{methyl}$) (n=5) obtained under the aforementioned conditions was 23.46. $Ct_{methyl}$ reflects the amount of CD31 promoters, in which C at position 109 in the nucleotide sequence of SEQ ID NO: 1 had been methylated, contained in the genomic DNA of human ASCs ($I_{methyl}$).

The above extracted DNA sample was treated with the methylation-dependent restriction enzyme McrBC (New England Biolabs Japan Inc., M0272S), so that an (A/G)$^m$C sequence (wherein $^m$C indicates a methylated cytosine) was selectively cleaved. Using the McrBC-treated DNA as a template, and also using the first primer set, real-time PCR was carried out under the same conditions as described above. A mean value of the Ct values ($Ct_{no-methyl}$) (n=5) obtained under the aforementioned conditions was 32.75. $Ct_{no-methyl}$ reflects the amount of CD31 promoters, in which both C at position 79 and C at position 85 in the nucleotide sequence of SEQ ID NO: 1 had not been methylated, contained in the genomic DNA of human ASCs ($I_{no-methyl}$).

The above extracted DNA sample was treated with the methylation-non-sensitive restriction enzyme MspI (Takara Bio, Inc., 1150AH), so that all CCGG sequences were cleaved regardless of the methylation of C. Using the MspI-treated DNA as a template, and also using the first primer set, real-time PCR was carried out under the same conditions as described above. Since the CD31 promoter contained in human genomic DNA comprises a CCGG sequence at positions 108 to 111 in SEQ ID NO: 1, an amplification product should not have been generated under these conditions. Thus, this was used as a negative control. In reality, an amplification product could not be detected in a test of n=5, and the Ct value could not be obtained.

When the amplification rate in one cycle of PCR is set at E, the following formulae (1) and (2) are established:

$$I_{total} \times E^{Ct\ total} = I_{methyl} \times E^{Ct\ methyl} \qquad \text{Formula(1)}$$

$$I_{total} \times E^{Ct\ total} = I_{no-methyl} \times E^{Ct\ no-methyl} \qquad \text{Formula(2)}$$

The rate (%), in which C at position 109 of SEQ ID NO: 1 of CD31 promoter in the genomic DNA of human ASCs has been methylated (referred to as $C_{109}$ methylation rate), is represented by $100 \times I_{methyl}/I_{total}$, and this rate can be calculated by the above formula (1) to the following formula (3):

$$100 \times I_{methyl}/I_{total} = 100 \times E^{Ct\ total - Ct\ methyl} \qquad \text{Formula (3)}$$

Similarly, the rate (%), in which both C at position 79 and C at position 85 in the CD31 promoter in the genomic DNA of human ASCs had not been methylated (referred to as $C_{79}C_{85}$ unmethylation rate), is represented by $100 \times I_{no-methyl}/I_{total}$, and this rate can be calculated by the above formula (2) to the following formula (4):

$$100 \times I_{no-methyl}/I_{total} = 100 \times E^{Ct\ total - Ct\ no-methyl} \qquad \text{Formula (4)}$$

When the amplification rate E was set at 2, according to Formula (3), $C_{109}$ methylation rate (%)=$100 \times 2^{-0.02}$=98.62, which was almost 100%.

Moreover, according to Formula (4), $C_{79}C_{85}$ unmethylation rate (%)=$100 \times 2^{-9.31}$=0.16, which was almost 0%. From these results, it is also found that the rate, in which at least one of C at position 79 and C at position 85 in the first region is methylated ($C_{79}C_{85}$ methylation rate (%)), is 100−0.16=99.84%, which is almost 100%.

Experiment 2

DNA extracted from cultured ASCs was subjected to real-time PCR at n=5, using, as templates, four DNA samples, namely, samples without a restriction enzyme treatment, and with a treatment with HapII, McrBC and MspI, in the same manner as Experiment 1, with the exception that the second primer set was used as a primer set. $Ct_{total}$, $Ct_{methyl}$, $Ct_{no-methyl}$ were obtained as mean values. $Ct_{total}$, $Ct_{methyl}$, and $Ct_{no-methyl}$ were found to be 23.51, 23.52, and 33.91, respectively. In the case of the MspI treatment, an amplification product could not be detected, and the Ct value could not be obtained.

The $Ct_{methyl}$ in Experiment 2 reflects the amount of CD31 promoters in which C at position 157 in the nucleotide sequence of SEQ ID NO: 1 has been methylated, contained in the genomic DNA of human ASCs. The $Ct_{no-methyl}$ in Experiment 2 reflects the amount of CD31 promoters in which C at position 191 in the nucleotide sequence of SEQ ID NO: 1 has not been methylated, contained in the genomic DNA of human ASCs.

The rate (%) in which C at position 157 of SEQ ID NO: 1 of CD31 promoter in the genomic DNA of human ASCs had been methylated (referred to as $C_{157}$ methylation rate), which was obtained as with Experiment 1, was 100%, and the rate (%) in which C at position 191 had been methylated (referred to as $C_{191}$ unmethylation rate) was 0.07%, which was almost 0%.

Experiment 3

DNA extracted from cultured ASCs was subjected to real-time PCR at n=5, using, as templates, two DNA samples, namely, samples without a restriction enzyme treatment and with a treatment with HapII, in the same manner as Experiment 1, with the exception that the third primer set was used as a primer set. $Ct_{to}$ land $Ct_{methyl}$ were obtained as mean values. $Ct_{total}$ and $Ct_{methyl}$ were found to be 24.21 and 24.87, respectively.

The $Ct_{methyl}$ in Experiment 3 reflects the amount of CD31 promoters in which C at position 200 in the nucleotide sequence of SEQ ID NO: 1 has been methylated, contained in the genomic DNA of human ASCs.

The rate (%) in which C at position 200 of SEQ ID NO: 1 of CD31 promoter in the genomic DNA of human ASCs had been methylated (referred to as $C_{200}$ methylation rate), which was obtained as with Experiment 1, was 63%.

Experiment 4

DNA extracted from cultured ASCs was subjected to real-time PCR at n=5, using, as templates, two DNA samples, namely, samples without a restriction enzyme treatment and with a treatment with HapII, in the same manner as Experiment 1, with the exception as that the fourth primer set was used a primer set. $Ct_{total}$ was obtained as a mean value. $Ct_{total}$ and $Ct_{methyl}$ were found to be 21.30 and 22.35, respectively.

The $Ct_{methyl}$ in Experiment 4 reflects the amount of CD31 promoters in which C at position 218 in the nucleotide sequence of SEQ ID NO: 1 has been methylated, contained in the genomic DNA of human ASCs.

The rate (%) in which C at position 218 of SEQ ID NO: 1 of CD31 promoter in the genomic DNA of human ASCs had been methylated (referred to as $C_{218}$ methylation rate), which was obtained as with Experiment 1, was 48%.

Experiment 5

Adipose tissues are treated with collagenase, so that they can be separated into mature adipocytes and a stromal vascular fraction (SVF). SVF comprises vascular endothelial cells, pericytes, and blood-derived cells (leucocytes, erythrocytes, and monocytes), as well as ASCs. In general, adipose tissues comprise approximately 10% of mature adipocytes, approximately 35% of ASCs, approximately 10% of vascular endothelial cells, approximately 10% of pericytes, and approximately 35% of blood vessel-derived cells, relative to the cell count.

Genomic DNA was extracted from individual cells by the same methods as Experiment 1 to Experiment 4, and the $C_{109}$ methylation rate, $C_{157}$ methylation rate, $C_{200}$ methylation rate and $C_{218}$ methylation rate in individual cells were obtained. The individual methylation rates in ASCs indicate the values obtained in Experiment 1 to 4.

Mature adipocytes were induced and prepared from cultured ASCs used in Experiment 1 to Experiment 4, using StemPre® Adipogenesis Differentiation Kit (Life Technologies Japan Ltd., A10070-01). The induction treatment (3 weeks) was carried out in accordance with the instruction manual, and the cells were then peeled by treating them with TrypLE™ Select (Life Technologies Japan Ltd., 12563029) (37° C., 10 minutes). The cell suspension was centrifuged (800 g, 5 minutes), and only the floating cells were then recovered, so as to obtain mature adipocytes with high purity (almost 100%).

As vascular endothelial cells, commercially available cell pellets (D11018) of human umbilical vein endothelial cells (HUVEC) were purchased from Takara Bio, Inc.

As pericytes, commercially available cell pellets (D11075) of human placenta-derived pericytes (hPC-PL) were purchased from Takara Bio, Inc.

Blood-derived cells were prepared by centrifuging blood provided from a volunteer, from whom a consent was obtained.

TABLE 1

| Cell type | | Methylation rate (%) | | | |
|---|---|---|---|---|---|
| | | $C_{109}$ | $C_{157}$ | $C_{200}$ | $C_{218}$ |
| SVF components | ASC | 100 | 100 | 63 | 48 |
| | Vascular endothelial cells | 2 | 3 | 12 | 3 |
| | Pericytes | 57 | 2 | 19 | 5 |
| | Blood-derived cells | 33 | 4 | 3 | 3 |
| Mature adipocytes | | 73 | 4 | 28 | 19 |

As shown in the above table, it became clear that the methylation rate of C at positions 109, 157, 200 and 218 in the sequence (SEQ ID NO: 1) of CD31 promoter in the genomic DNA of human ASCs is significantly higher than in the genomic DNA of other cells contained in adipose tissues or SVF. As a result, it became clear that, as an indicator for evaluating the content of ASCs in a sample consisting of adipose tissues or SVF, the amount of the methylated C at positions 109, 157, 200 and 218, contained in genomic DNA extracted from the sample, is effective, that the amount of the methylated C at positions 157, 200 and 218 is more effective, and that the amount of the methylated C at position 157 is particularly effective.

Experiment 6

SVF obtained from human adipose tissues was used as a sample, and the amount of the methylated C at position 157 in the CD31 promoter sequence (SEQ ID NO: 1) of genomic DNA was used as an indicator, so that the content of ASCs in the sample was evaluated. For comparison, the amount of ASCs in the above-described sample was obtained by flow cytometry.

SVF was prepared by treating human adipose tissues provided from three volunteers with collagenase (Wako Pure Chemical Industries, Ltd., 038-22361) (37° C., 30 minutes) and then centrifuging them (800 g, 5 minutes). SVFs prepared from the adipose tissues of the three volunteers were defined as #1, #2, and #3, respectively.

Cultured ASCs used for producing a calibration curve were prepared by the same method as Experiment 1.

Genomic DNA was extracted from SVF, using Nucleo-Spin® Tissue (Takara Bio, Inc., U0952S), and operations were carried out in accordance with the protocols included therewith.

In the same manner as in the above-described Experiment 2, using the sample treated with the restriction enzyme HapII as a template, genomic DNA extracted from SVF was subjected to real-time PCR using the second primer set, and thereafter, the $Ct_{methyl}$ value was obtained. Using a calibration curve showing the correlation between the $Ct_{methyl}$ value and the cell count of ASCs, which was produced by the following procedures, the cell count of ASCs was estimated from the $Ct_{methyl}$ value.

The calibration curve was produced by the following procedures. The cell count of the above prepared cells for calibration curve was measured using NucleoCounter NC-200 (manufactured by Chemometec), and the cells were prepared to the cell amounts of $3.3 \times 10^6$, $1.7 \times 10^6$, $8.3 \times 10^5$, $4.1 \times 10^5$, $2.0 \times 10^5$, $1.0 \times 10^5$, $5.0 \times 10^4$, $2.5 \times 10^4$, $1.3 \times 10^4$, and $6.5 \times 10^3$ (cells). Genomic DNA was extracted from each sample, using NucleoSpin® Tissue (Takara Bio, Inc., U0952S), and the operations were carried out in accordance with the protocols included therewith. In the same manner as in the above-described Experiment 2, using the sample treated with the restriction enzyme HapII as a template, the extracted genomic DNA was subjected to real-time PCR using the second primer set, and thereafter, the $Ct_{methyl}$ value was obtained. Thereafter, a calibration curve showing the correlation between the $Ct_{methyl}$ value and the cell count of ASCs was produced.

The amount of ASCs in the SVF sample was obtained by flow cytometry according to the following procedures. First, the total cell count ($C_{All}$) in the SVF sample was measured using NucleoCounter NC-200 (manufactured by Chemometec). Subsequently, the SVF sample was double-stained with a CD34-PE (BD Pharmingen, 348057) antibody and a CD31-FITC (BD Pharmingen, 553372) antibody, and thereafter, the rate of CD31-negative/CD34-positive cells ($P_{ASCs}$, %), which are characteristic for ASCs, was measured by flow cytometry (FACS Calibur, BD Bioscience). The amount of ASCs in the SVF sample can be calculated according to the following formula (5).

$$C_{All} \times P_{ASCs}/100 = \text{Amount of ASCs in SVF sample} \quad \text{Formula(5)}$$

The results are shown in the following Table 2.

TABLE 2

| | SVF | The present invention (PCR method) | Flow cytometry | The present invention/ flow cytometry |
|---|---|---|---|---|
| Number of ASCs ($\times 10^5$ cells/ 1 mL adipose tissues) | #1 | 1.9 | 2.3 | 0.8 |
| | #2 | 1.5 | 1.6 | 0.9 |
| | #3 | 3.8 | 3.6 | 1.1 |

INDUSTRIAL APPLICABILITY

The present invention has high utility value in the technical field of using mesenchymal stem cells, such as regenerative medicine.

All publications, patents and patent applications cited in the present description are incorporated herein by reference in their entirety.

The invention claimed is:

1. A method comprising:
obtaining a sample comprising a stromal vascular fraction (SVF) obtained from an adipose tissue, wherein the SVF obtained from the adipose tissue includes mesenchymal stem cells;
detecting a nucleotide sequence in genomic DNA obtained from the sample; and
determining a content of the mesenchymal stem cells in the sample from the detected nucleotide sequence by counting and quantifying the number of mesenchymal stem cells in the sample,
wherein the nucleotide sequence comprises at least one CpG site selected from the group consisting of: a CpG site consisting of C at position 157 and G at position 158 of SEQ ID NO: 1; and a CpG site complementary to the CpG site of SEQ ID NO: 1 in a nucleotide sequence complementary to the nucleotide sequence of SEQ ID NO: 1; and
wherein detecting the nucleotide sequence comprises:
selectively detecting an amount of DNA comprising the nucleotide sequence, wherein the at least one CpG site is methylated.

2. The method according to claim 1, wherein the sample is a stromal vascular fraction obtained from an adipose tissue.

3. The method according to claim 1, further comprising, prior to detecting the nucleotide sequence, subjecting the genomic DNA to a restriction enzyme treatment.

4. The method according to claim 3, wherein a restriction enzyme used in the restriction enzyme treatment is an enzyme specifically cleaving only a methylated nucleotide sequence, or an enzyme that has CCGG as a recognition sequence and cannot cleave a methylated nucleotide sequence.

5. The method according to claim 3, further comprising, prior to detecting the nucleotide sequence, performing a nucleic acid amplification using the genomic DNA subjected to the restriction enzyme treatment.

6. A method comprising:
selecting a sample; and
producing a mesenchymal stem cell-containing formulation from the selected sample,
wherein selecting the sample comprises detecting a nucleotide sequence in genomic DNA obtained from the sample,
wherein the nucleotide sequence comprises at least one CpG site selected from the group consisting of: a CpG site consisting of C at position 157 and G at position 158 of SEQ ID NO: 1; and a CpG site complementary to the CpG site of SEQ ID NO: 1 in a nucleotide sequence complementary to the nucleotide sequence of SEQ ID NO: 1, and
wherein the sample is an adipose tissue or a cell-containing fraction obtained from an adipose tissue.

7. The method according to claim 6, wherein the sample is a stromal vascular fraction obtained from an adipose tissue.

8. The method according to claim 6, wherein producing the mesenchymal stem cell-containing formulation comprises combining the selected sample with matured adipose cells to prepare a cell-containing composition.

9. The method according to claim 6, wherein selecting the sample comprises:
selectively detecting an amount of DNA comprising the nucleotide sequence, wherein the at least one CpG site is methylated; or
selectively detecting an amount of DNA comprising the nucleotide sequence, wherein the at least one CpG site is not methylated.

10. The method according to claim 6, wherein selecting the sample further comprises, prior to detecting the nucleotide sequence, subjecting the genomic DNA to a restriction enzyme treatment.

11. The method according to claim 10, wherein a restriction enzyme used in the restriction enzyme treatment is an enzyme specifically cleaving only a methylated nucleotide sequence, or an enzyme that has CCGG as a recognition sequence and cannot cleave a methylated nucleotide sequence.

12. The method according to claim 10, wherein producing the mesenchymal stem cell-containing formulation comprises combining the selected sample with matured adipose cells to prepare a cell-containing composition.

13. A method comprising:
  detecting a nucleotide sequence in genomic DNA obtained from a first human adipose tissue-derived stromal vascular fraction (SVF) and a first tissue comprising mature adipocytes;
  determining a content of human adipose tissue-derived mesenchymal stem cells (ASCs) in the first SVF and a content of the ASCs in the first tissue comprising mature adipocytes from the detected nucleotide sequence, wherein the content of ASCs in the first SVF is the number of ASCs in the first SVF, and the content of ASCs in the first tissue comprising mature adipocytes is the number of ASCs in the first tissue comprising adipocytes;
  determining the amount ratio between the first SVF and the first tissue comprising mature adipocytes, based on the content of the ASCs in the first SVF and the content of the ASCs in the first tissue comprising mature adipocytes;
  producing a first adipose tissue by combining the first SVF with the first tissue comprising mature adipocytes according to the amount ratio; and
  transplanting the first adipose tissue into a human,
  wherein the nucleotide sequence comprises at least one CpG site selected from the group consisting of: a CpG site consisting of C at position 157 and G at position 158 of SEQ ID NO: 1; and a CpG site complementary to the CpG site of SEQ ID NO: 1 in a nucleotide sequence complementary to the nucleotide sequence of SEQ ID NO: 1; and
  wherein detecting the nucleotide sequence comprises:
    selectively detecting an amount of DNA comprising the nucleotide sequence, wherein the at least one CpG site is methylated.

14. The method according to claim 13, further comprising culturing the first SVF prior to producing the first adipose tissue.

15. The method according to claim 13, further comprising, after transplanting the first adipose tissue:
  predicting an amount of a second SVF derived from a human adipose tissue and an amount of the human adipose tissue necessary for preparation of the second SVF, based on the content of the ASCs in the first SVF or the content of the ASCs in the first tissue comprising mature adipocytes;
  producing a second adipose tissue by combining the second SVF with a second tissue comprising mature adipocytes; and
  transplanting the second adipose tissue into the human.

16. The method according to claim 13, further comprising:
  obtaining a second SVF derived from a human adipose tissue by culturing at least a part of the first SVF before or after producing the first adipose tissue;
  producing a second adipose tissue, after transplanting the first adipose tissue, by combining the second SVF with a second tissue comprising mature adipocytes; and
  transplanting the second adipose tissue into the human.

17. A method comprising:
  obtaining a human adipose tissue-derived stromal vascular fraction (SVF) derived from a human adipose tissue, wherein the SVF includes human adipose tissue-derived mesenchymal stem cells (ASCs);
  detecting a nucleotide sequence in genomic DNA obtained from the human adipose tissue-derived stromal vascular fraction (SVF) derived from the human adipose tissue;
  determining a content of human adipose tissue-derived mesenchymal stem cells (ASCs) in the SVF from the detected nucleotide sequence by counting and quantifying the number of ASCs in the SVF;
  determining conditions for culturing the SVF, based on the content of the ASCs in the SVF, wherein determining conditions for culturing the SVF, including determining culture time and number of subcultures, allows SVF to be obtained; and
  culturing the SVF under the determined conditions,
  wherein the nucleotide sequence comprises at least one CpG site selected from the group consisting of: a CpG site consisting of C at position 157 and G at position 158 of SEQ ID NO: 1; and a CpG site complementary to the CpG site of SEQ ID NO: 1 in a nucleotide sequence complementary to the nucleotide sequence of SEQ ID NO: 1; and
  wherein detecting the nucleotide sequence comprises:
    selectively detecting an amount of DNA comprising the nucleotide sequence, wherein the at least one CpG site is methylated.

18. A method comprising:
  obtaining a human adipose tissue-derived stromal vascular fraction (SVF), wherein the SVF includes human adipose tissue-derived mesenchymal stem cells (ASCs);
  detecting a nucleotide sequence in genomic DNA obtained from the human adipose tissue-derived stromal vascular fraction (SVF); and
  determining a content of human adipose tissue-derived mesenchymal stem cells (ASCs) or a content of cells other than the ASCs in the SVF from the detected nucleotide sequence by counting and quantifying the number of ASCs in the SVF,
  wherein the nucleotide sequence comprises at least one CpG site selected from the group consisting of: a CpG site consisting of C at position 157 and G at position 158 of SEQ ID NO: 1; and a CpG site complementary to the CpG site of SEQ ID NO: 1 in a nucleotide sequence complementary to the nucleotide sequence of SEQ ID NO: 1; and
  wherein detecting the nucleotide sequence comprises:
    selectively detecting an amount of DNA comprising the nucleotide sequence, wherein the at least one CpG site is methylated.

* * * * *